(12) United States Patent
Schmidt et al.

(10) Patent No.: US 7,657,315 B2
(45) Date of Patent: Feb. 2, 2010

(54) IMPLANTABLE MEDICAL DEVICE WITH A DUAL POWER SOURCE

(75) Inventors: Craig L. Schmidt, Eagan, MN (US); Paul M. Skarstad, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 349 days.

(21) Appl. No.: 11/622,313

(22) Filed: Jan. 11, 2007

(65) Prior Publication Data

US 2007/0162083 A1    Jul. 12, 2007

Related U.S. Application Data

(60) Division of application No. 10/057,419, filed on Jan. 25, 2002, now Pat. No. 7,191,008, which is a continuation-in-part of application No. 09/870,097, filed on May 30, 2001, now Pat. No. 6,650,942.

(51) Int. Cl.
*A61N 1/08* (2006.01)

(52) U.S. Cl. .......................................... 607/29; 607/34
(58) Field of Classification Search .................... 607/34
See application file for complete search history.

(56) References Cited

U.S. PATENT DOCUMENTS

| | | |
|---|---|---|
| 3,981,309 A | 9/1976 | Cannon |
| 4,310,000 A | 1/1982 | Lindemans |
| 4,375,817 A | 3/1983 | Engle et al. |
| 4,612,100 A | 9/1986 | Edeling et al. |
| 4,964,877 A | 10/1990 | Kiester et al. |
| 5,147,737 A | 9/1992 | Post et al. |
| 5,221,453 A | 6/1993 | Crespi et al. |
| 5,235,979 A | 8/1993 | Adams |
| 5,250,373 A | 10/1993 | Muffoletto et al. |
| 5,306,581 A | 4/1994 | Taylor et al. |
| 5,312,458 A | 5/1994 | Muffoletto et al. |
| 5,331,966 A | 7/1994 | Bennett et al. |
| 5,333,095 A | 7/1994 | Stevenson et al. |
| 5,372,605 A | 12/1994 | Adams et al. |
| 5,434,017 A | 7/1995 | Berkowitz et al. |
| 5,439,760 A | 8/1995 | Howard et al. |
| 5,458,997 A | 10/1995 | Crespi |
| 5,468,569 A | 11/1995 | Pyszczek et al. |

(Continued)

FOREIGN PATENT DOCUMENTS

DE    4112936 A1    10/1991

(Continued)

OTHER PUBLICATIONS

Crespi et al., "evolution of Power Sources for Implantable Cardioverter Defibrillators", Journal of Power Sources, Elsevier, Amsterdam, NL, vol. 96, No. 1, Jun. 1, 2001. pp. 33-38.

*Primary Examiner*—Kennedy J Schaetzle

(57) ABSTRACT

An implantable medical device includes a control circuit for controlling the operation of the device and for obtaining physiological data from a patient in which the medical device is implanted. The implanted device also includes a communication circuit for transmitting the physiological data to an external device. A first power source is coupled to the control circuit and provides power to the control circuit. A second power source is coupled to the communication circuit and provides power to the communication circuit.

3 Claims, 13 Drawing Sheets

U.S. PATENT DOCUMENTS

| | | |
|---|---|---|
| 5,549,717 A | 8/1996 | Takeuchi et al. |
| 5,614,331 A | 3/1997 | Takeuchi et al. |
| 5,716,729 A | 2/1998 | Sunderland et al. |
| 5,836,992 A | 11/1998 | Thompson et al. |
| 6,184,324 B1 | 2/2001 | Benz et al. |
| 6,456,883 B1 * | 9/2002 | Torgerson et al. ............. 607/34 |
| 6,650,942 B2 | 11/2003 | Howard et al. |
| 2002/0183800 A1 | 12/2002 | Schmidt et al. |
| 2003/0096163 A1 | 5/2003 | Miyake et al. |

FOREIGN PATENT DOCUMENTS

| | | |
|---|---|---|
| DE | 19942021 | 3/2001 |
| WO | WO0234442 | 5/2002 |

* cited by examiner

IMPLANTABLE MEDICAL DEVICE WITH A DUAL POWER SOURCE

PRIORITY CLAIM

This Application is a divisional application of U.S. patent application Ser. No. 10/057,419, entitled "Implantable Medical Device With a Dual Power Source," filed Jan. 25, 2002 now U.S. Pat. No. 7,191,008; which is a continuation-in-part of Ser. No. 09/870,097 filed May 30, 2001, now U.S. Pat. No. 6,650,942, granted Nov. 18, 2003, entitled "Implantable Medical Device With a Dual Cell Power Source," which is incorporated herein by reference in its entirety.

BACKGROUND OF THE INVENTION

The present invention relates generally to a power source for an implantable medical device, and more particularly, the present invention relates to a dual cell power source for optimizing implantable medical device performance.

A variety of different implantable medical devices (IMDs) are available for therapeutic stimulation of the heart and are well known in the art. For example, implantable cardioverter-defibrillators (ICDs) are used to treat those patients suffering from ventricular fibrillation, a chaotic heart rhythm that can quickly result in death if not corrected. In operation, the ICD continuously monitors the electrical activity of a patient's heart, detects ventricular fibrillation, and in response to that detection, delivers appropriate shocks to restore normal heart rhythm. Similarly, an automatic implantable defibrillator (AID) is available for therapeutic stimulation of the heart. In operation, an AID device detects ventricular fibrillation and delivers a non-synchronous high-voltage pulse to the heart through widely spaced electrodes located outside of the heart, thus mimicking transthoratic defibrillation. Yet another example of a prior art cardioverter includes the pacemaker/cardioverter/defibrillator (PCD) disclosed, for example, in U.S. Pat. No. 4,375,817 to Engle, et al. This device detects the onset of tachyarrhythmia and includes means to monitor or detect progression of the tachyarrhythmia so that progressively greater energy levels may be applied to the heart to interrupt a ventricular tachycaria or fibrillation. Numerous other, similar implantable medical devices, for example a programmable pacemaker, are further available.

Regardless of the exact construction and use, each of the above-described IMDs generally includes three primary components: a low-power control circuit, a high-power output circuit, and a power source. The control circuit monitors and determines various operating characteristics, such as, for example, rate, synchronization, pulse width and output voltage of heart stimulating pulses, as well as diagnostic functions such as monitoring the heart. Conversely, the high-power output circuit generates electrical stimulating pulses to be applied to the heart via one or more leads in response to signals from the control circuit.

The power source provides power to both the low-power control circuit and the high-power output circuit. As a point of reference, the power source is typically required to provide 10-20 microamps to the control circuit and a higher current to the output circuit. Depending upon the particular IMD application, the high-power output circuit may require a stimulation energy of as little as 0.1 Joules for pacemakers to as much as 40 Joules for implantable defibrillators. In addition to providing a sufficient stimulation energy, it is desirable that the power source possess a low self-discharge to have a useful life of many years, and that it is highly reliable, and able to supply energy from a minimum packaged volume.

Suitable power sources or batteries for IMD's are virtually always electrochemical in nature, commonly referred to as electrochemical cells. Acceptable electrochemical cells for IMDs typically include a case surrounding an anode, a separator, a cathode and an electrolyte. The anode material is typically a lithium metal or, for rechargeable cells, a lithium ion containing body. Lithium batteries are generally regarded as acceptable power sources due in part to their high energy density and low self-discharge characteristics relative to other types of batteries. The cathode material is typically metal-based, such as silver vanadium oxide (SVO), manganese dioxide, etc.

In some cases, the power requirements of the output circuit are higher than the battery can deliver. Thus, it is common in the prior art to accumulate and store the stimulating pulse energy in an output energy storage device at some point prior to the delivery of a stimulating pulse, such as with an output capacitor. When the control circuit indicates to the output circuit that a stimulating pulse is to be delivered, the output circuitry causes the energy stored in the output capacitor to be applied to the cardiac tissue via the implanted leads. Prior to delivery of a subsequent stimulating pulse, the output capacitor is typically recharged, with the time required for the power source to recharge the output capacitor being referred to as the "charge time".

Regardless of whether an output capacitor(s) is employed, one perceived drawback of currently known therapeutic pulsing IMDs is that they often have to be replaced before their battery depletion levels have reached a maximum. When an IMD's output capacitor is being recharged, there is a drop in battery voltage due to the charging current flowing through an inherent battery impedance. Although this voltage drop may not be significant when the battery is new or fresh, it may increase substantially as the battery ages or is approaching depletion, such that during a capacitor recharging operation, the voltage supply to the control circuit may drop below a minimum allowable level. This temporary drop can cause the control circuit to malfunction. The IMD may be removed and replaced before any such malfunctions occur, even though the battery may still have sufficient capacity to stimulate the heart. Simply stated, the rate capability of currently available lithium-based cells is highly dependent upon time or depth-of-discharge as the cell develops high internal resistance over time and/or with repeated use. For IMD applications, this time or depth-of-discharge dependence limits the battery's useful life.

One solution to the above-described issue is to provide two batteries, one for charging the output circuit or capacitor and a separate battery for powering the control circuit. Unfortunately, the relative amounts of energy required by the device for the control and charging/output circuitry tend to vary from patient to patient. The capacity of the battery to power the control circuit can only be optimized with regard to one patient profile. Thus for other patients, one battery may deplete before the other, leaving wasted energy in the device. An example of such a system is disclosed in U.S. Pat. No. 5,614,331 to Takeuchi et al.

An additional, related concern associated with IMD power sources relates to overall size constraints. In particular, in order to provide an appropriate power level for a relatively long time period (on the order of 4-7 years), the power source associated with the high-power output circuitry typically has a certain electrode surface area to achieve the high-rate capability. Due to safety and fabrication constraints, the requisite electrode surface area can be achieved with an increased cell volume. The resulting cell may satisfy output circuitry power requirements, but unfortunately may be volumetrically inefficient. Even further, recent IMD designs require the power source to assume a shape other than rectangular, such as a "D" or half "D" contour, further contributing to volumetric inefficiencies.

In general terms, then, currently available electrochemical cell designs, especially Li/SVO constructions, may satisfy, at least initially, power requirements for the output circuitry. The inherent volumetric inefficiencies of these cells, however, dictates an end-of-life point at which less than the cell's useful capacity has been used. Once again, currently available cells exhibit an output circuitry charge time that is highly dependent upon time of use or depth-of-discharge. Over time, the cell's impedance increases, thereby increasing the resulting charge time. Virtually all IMDs have a maximum allowable charge time for the output circuitry. Once the cell's charge time exceeds the maximum allowable charge time, the IMD may be replaced. The volumetrically inefficient cell may quickly reach this maximum charge time, even though a large portion of the cell's capacity remains unused (on the order of 40% of the useful capacity). Thus, regardless of whether the power source incorporates one or two cells, the resulting configuration is highly inefficient in terms of the high-rate battery's useful capacity.

Manufacturers continue to improve upon IMD construction and size characteristics. To this end, currently available power source designs are less than optimal. Therefore, a need exists for an IMD power source having superior space-volumetric efficiencies and a higher energy density, without a proportional increase in charge time.

Yet another issue associated with IMD power sources involves the use of a wireless transceiver to communicate IMD data with an external device. The data communicated by the IMD may include physiological data related to the patient in which the IMD is implanted. For example, if the IMD is a pacemaker or cardioverter/defibrillator, the physiological data may include electric cardiac signals obtained from electrodes implanted within the patient's heart as previously discussed. The external device with which the IMD communicates this physiological data may include a computer, for example, that monitors and/or processes the physiological data that is received from the IMD.

The IMD may also communicate data related to its performance, such as the intensity level in which it delivered a therapeutic shock for a given set of electric cardiac signals monitored via the implanted electrodes. The external computer device may analyze the received data and transmit programming data to the IMD to adjust its therapy. For example, the programming data may indicate to the IMD to reduce the intensity of the therapeutic shock delivered to the patient.

Typically, the wireless transceiver within the IMD requires relatively high current pulses, thus resulting in a higher drain from the power source within the IMD. As the sophistication of the IMD and the number of communication transmissions performed by the IMD is expected to increase over the next several years, a much higher burden may be placed on the IMD's power source, thus reducing its life. Because the accessibility of the power source is achieved typically via a surgical procedure, this reduction in battery life is a concern.

The present invention is directed to reducing the effects of one or more of the problems set forth above.

SUMMARY OF THE INVENTION

According to the present invention, an apparatus includes a control circuit coupled to a first power source to control the operation of the apparatus, the control circuit being adapted to receive power from the first power source. A communication circuit is coupled to a second power supply to communicate with an external device, the communication circuit being adapted to receive power from the second power source.

According to the present invention, an implantable medical device includes a control circuit to control the operation of implantable the medical device and to obtain physiological data from a patient in which the implantable medical device is implanted. A communication circuit is coupled to the control circuit to transmit the physiological data to an external device, a first power source is coupled to the control circuit to provide power to the control circuit, and a second power source is coupled to the communication circuit to provide power to the communication circuit.

According to the present invention, a method for incorporating a power source in an implantable medical device includes providing power to a control circuit by a first power source, the control circuit obtaining physiological data of a patient in which at least the control circuit is implanted; providing power to a communication circuit by a second power source; and transmitting the physiological data from the communication circuit to an external device.

DETAILED DESCRIPTION OF THE PREFERRED EMBODIMENTS

Figure 1:
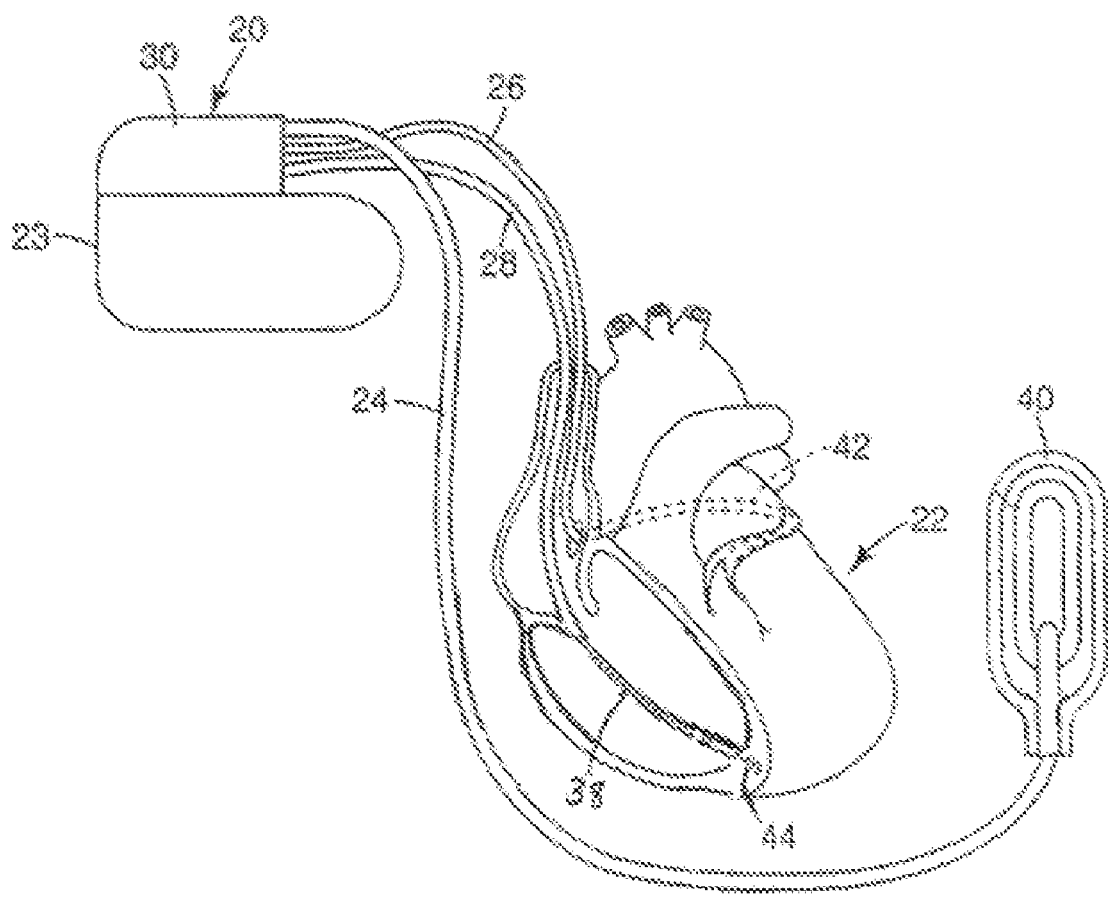
FIG. 1 is a simplified schematic view of one embodiment of an implantable medical device (IMD) incorporating a power source in accordance with the present invention.

FIG. 1 is a simplified schematic view of one embodiment of an implantable medical device ("IMD") 20 in accordance with the present invention and its relationship to a human heart 22. The IMD 20 is shown in FIG. 1 as preferably being a pacemaker/cardioverter/defibrillator (PCD), although the IMD may alternatively be a drug delivery device, a neurostimulator, or any other type of implantable device known in the art. The IMD includes a case or hermetic enclosure 23 and associated electrical leads 24, 26 and 28. As described in greater detail below, the enclosure case 23 contains various circuits and a power source. The leads 24, 26 and 28 are coupled to the IMD 20 by means of a multi-port connector block 30, which contains separate ports for each of the three leads 24, 26, and 28 illustrated.

In one embodiment, lead 24 is coupled to a subcutaneous electrode 40, which is intended to be mounted subcutaneously in the region of the left chest. Alternatively, an active "can" may be employed such that stimulation is provided between an implanted electrode and enclosure case 23. In yet another embodiment, stimulation is provided between two electrodes carried on a single multipolar lead.

The lead 26 is a coronary sinus lead employing an elongated coil electrode that is located in the coronary sinus and great vein region of the heart 22. The location of the electrode is illustrated in broken line format at 42, and extends around the heart 22 from a point within the opening of the coronary sinus to a point in the vicinity of the left atrial appendage.

Lead 28 is provided with an elongated electrode coil 38 which is located in the right ventricle of the heart 22. The lead 28 also includes a helical stimulation electrode 44 which takes the form of an extendable/retractable helical coil which is screwed into the myocardial tissue of the right ventricle. The lead 28 may also include one or more additional electrodes for near and far field electrogram sensing.

In the system illustrated, cardiac pacing pulses are delivered between the helical electrode 44 and the coil electrode 38. The electrodes 38 and 44 are also employed to sense electrical signals indicative of ventricular contractions. Additionally, cardioverters/defibrillation shocks may be delivered between coil electrode 38 and the electrode 40, and between coil electrode 38 and electrode 42. During sequential pulse defibrillation, it is envisioned that pulses would be delivered sequentially between subcutaneous electrode 40 and coil electrode 38, and between the coronary sinus electrode 42 and coil electrode 38. Single pulse, two electrode defibrillation pulse regimens may also be provided, typically between coil electrode 38 and the coronary sinus electrode 42. Alternatively, single pulses may be delivered between electrodes 38 and 40. The particular interconnection of the electrodes to the IMD 20 will depend somewhat on the specific single electrode pair defibrillation pulse regimen is believed more likely to be employed.

Figure 2:
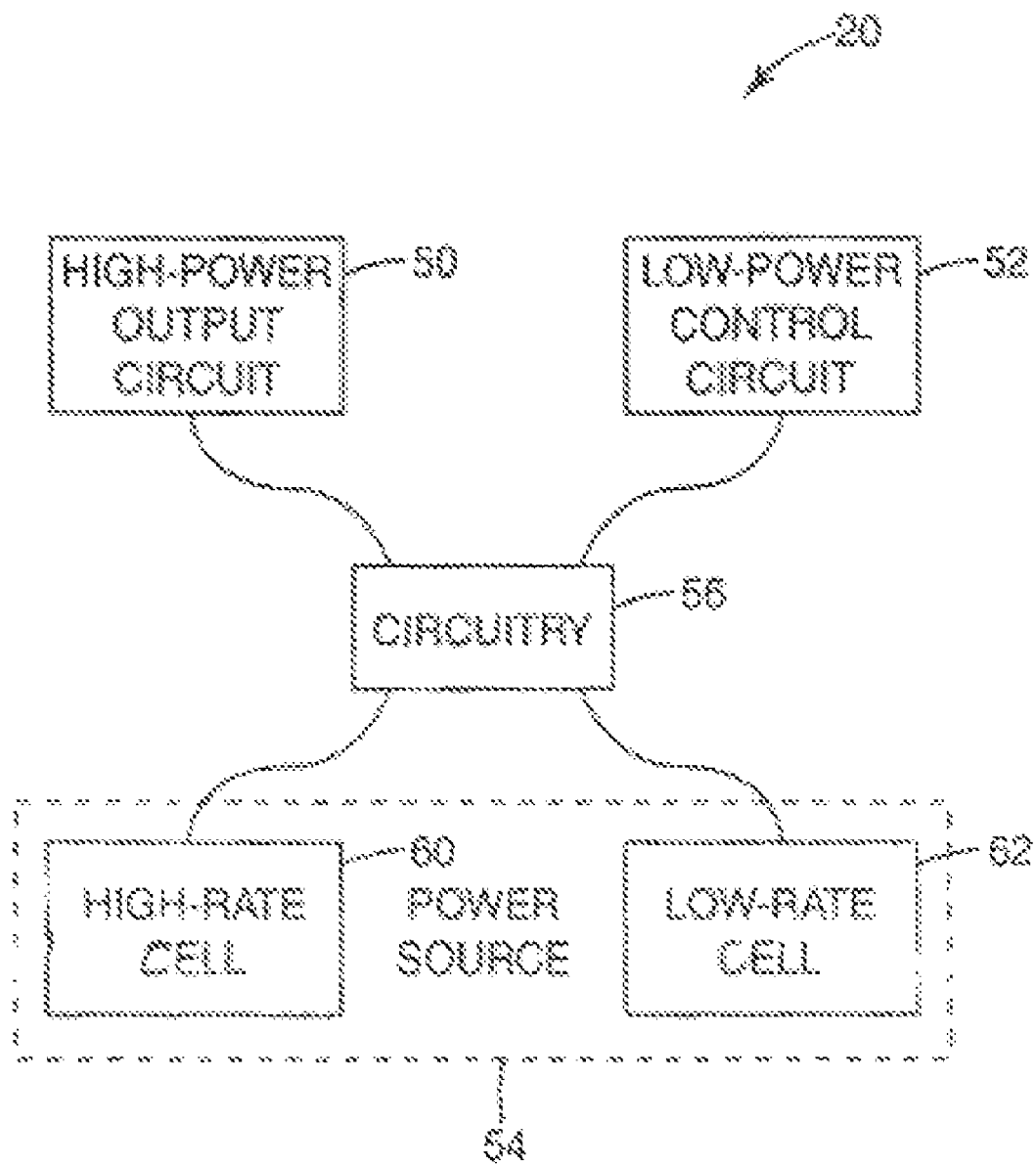
FIG. 2 is a simplified schematic circuit diagram of a power source in accordance with the present invention for use with the IMD of FIG. 1.

Regardless of the exact configuration and operation of the IMD 20, the IMD 20 includes several basic components, illustrated in block form in FIG. 2. The IMD 20 includes a high-power output circuit 50, a low-power control circuit 52, a power source 54 (shown with dashed lines) and circuitry 56. As described in greater detail below, the power source 54 is preferably a dual-cell configuration, and can assume a wide variety of forms. Similarly, the circuitry 56 can include analog and/or digital circuits, can assume a variety of configurations, and electrically connects the power source 54 to the high power circuit 50 and the low-power circuit 52.

The high-power output circuit 50 and the low-power control circuit 52 are typically provided as part of an electronics module associated with the IMD 20. In general terms, the high-power output circuit 50 is configured to deliver an electrical pulse therapy, such as a defibrillation or a cardioversion/defibrillation pulse. In sum, the high-power output circuit 50 is responsible for applying stimulating pulse energy between the various electrodes 38-44 (FIG. 1) of the IMD 20. As is known in the art, the high-power output circuit 50 may be associated with a capacitor bank (not shown) for generating an appropriate output energy, for example in the range of 0.1-40 Joules.

The low-power control circuit 52 is similarly well known in the art. In general terms, the low-power control circuit 52 monitors heart activity and signals activation of the high-power output circuit 50 for delivery of an appropriate stimulation therapy. Further, as known in the art, the low-power control circuit 52 may generate a preferred series of pulses from the high-power output circuit 50 as part of an overall therapy.

The power source 54 and associated circuitry 56 can assume a wide variety of configurations, as described in the various embodiments below. Preferably, however, the power source 54 includes a first, high-rate cell 60 and a second, lower-rate cell 62, such as a medium- or low-rate cell. Notably the first and second cells 60, 62 can be formed separate from one another or contained within a singular enclosure. Depending upon the particular application, the high-rate cell 60 is configured to provide a stimulation energy of as little as 0.1 Joules for pacemakers to as much as 40 Joules for implantable defibrillators. As described below with reference to specific embodiments, the high-rate cell 60 can assume a wide variety of forms as is known in the art. Preferably, the high-rate cell 60 includes an anode, a cathode and an electrolyte. The anode is preferably formed to include lithium, either in metallic form or ion form for re-chargeable applications. With this in mind, the high-rate cell 60 is most preferably a spirally-wound battery of the type disclosed, for example, in U.S. Pat. No. 5,439,760 to Howard et al. for "High Reliability Electrochemical Cell and Electrode Assembly Therefor" and U.S. Pat. No. 5,434,017 to Berkowitz et al. for "High Reliability Electrochemical Cell and Assembly Therefor," the disclosures of which are hereby incorporated by reference. The high-rate cell 60 may less preferably be a battery having a spirally-wound, stacked plate or serpentine electrodes of the type disclosed, for example, in U.S. Pat. Nos. 5,312,458 and 5,250,373 to Muffuletto et al. for "Internal Electrode and Assembly Method for Electrochemical Cells;" U.S. Pat. No. 5,549,717 to Takeuchi et al. for "Method of Making Prismatic Cell;" U.S. Pat. No. 4,964,877 to Kiester et al. for "Non-aqueous Lithium Battery;" U.S. Pat. No. 5,147,737 to Post et al. for "Electrochemical Cell With Improved Efficiency Serpentine Electrode;" and U.S. Pat. No. 5,468,569 to Pyszczek et al. for "Use of Standard Uniform Electrode Components in Cells of Either High or Low Surface Area Design," the disclosures of which are herein incorporated by reference. Alternatively, the high-rate cell 60 can include a single cathode electrode.

Materials for the cathode of the high-rate cell 60 are most preferably solid and comprise as active components thereof metal oxides such as vanadium oxide, silver vanadium oxide (SVO) or manganese dioxide, as is known in the art. Alternatively, the cathode for the high-rate cell 60 may also comprise carbon monoflouride and hybrids thereof or any other active electrolytic components and combination. Where SVO is employed for the cathode, the SVO is most preferably of the type known as "combination silver vanadium oxide" (or "CSVO") as disclosed in U.S. Pat. Nos. 5,221,453; 5,439,760; and 5,306,581 to Crespi et al, although other types of SVO may be employed.

It is to be understood that electrochemical systems other than those set forth explicitly above may also be utilized for the high-rate cell 60, including, but not limited to, anode/cathode systems such as lithium/silver oxide; lithium/manganese oxide; lithium/$V_2O_5$; lithium/copper silver vanadium oxide; lithium/copper oxide; lithium/lead oxide; lithium/carbon monoflouride; lithium/chromium oxide; lithium/bismuth-containing oxide; lithium/copper sulfate; mixtures of various cathode materials listed above such as a mixture of silver vanadium oxide and carbon monoflouride; and lithium ion re-chargeable batteries, to name but a few.

In general terms, the second, lower-rate cell 62 has a rate capability that is less than that of the high-rate cell 60, and is sufficient to power the low-power control circuit 52. For example, in one preferred embodiment, the second, lower-rate cell 62 is a medium rate, SVO cell, more preferably SVO/$CF_x$ cell. Alternatively, the second, lower-rate cell 62 can be a low-rate, lithium/iodine pacemaker battery having a current drain in the range of 10-30 microamps. As known in the art, acceptable constructions of the second, lower-rate cell 62 include, for example, a single cathode electrode design described in U.S. Pat. No. 5,716,729 to Sunderland et al. for "Electrochemical Cell," the disclosure of which is incorporated by reference. As used throughout the specification, reference to a "lower-rate cell" includes both a low-rate cell and a medium-rate cell. Regardless of the exact construction, the high rate cell 60 and the lower-rate cell 62 preferably have similar beginning of life (BOL) voltages (e.g., less than 100 mV). Further, it is preferred that the cells 60, 62 have similar depletion voltages so that the capacity of each of the cells 60, 62 is efficiently used when the first of the cells 60 or 62 reaches depletion.

Figure 3:
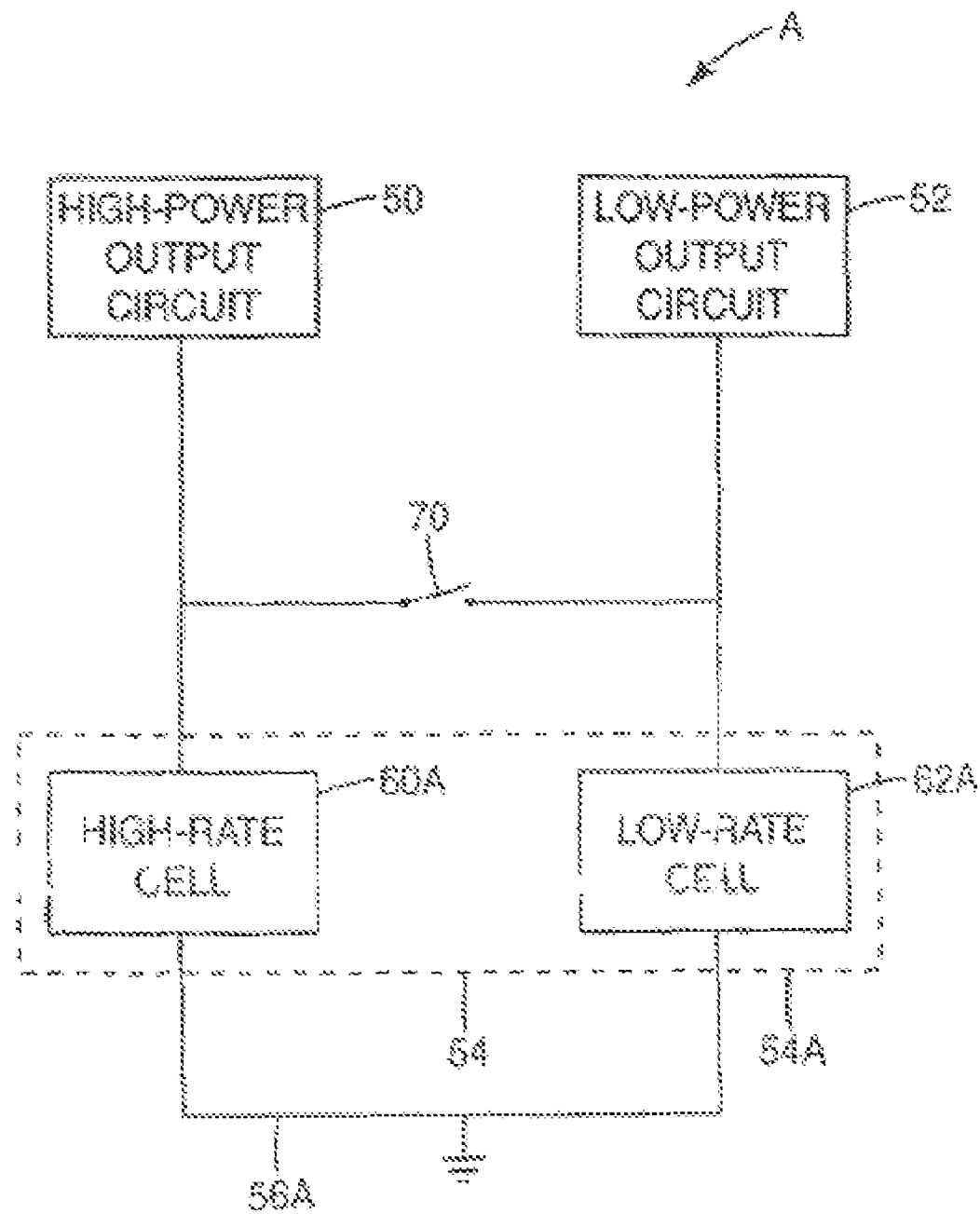
FIG. 3 is a simplified schematic diagram of a first embodiment power source in accordance with the present invention.

With the above-described parameters of the high-rate cell 60 and the second, lower-rate cell 62 in mind, one preferred combination A of a power source 54A and circuitry 56A is depicted schematically in FIG. 3. The power source 54A includes a first, high-rate cell 60A and a second, lower-rate cell 62A as described above. In addition, circuitry 56A electrically connects the high-rate cell 60A and the lower-rate cell 62A in parallel to the high-power output circuit 50 and the low-power control circuit 52. In particular, the circuitry 56A includes a switch 70 configured to selectively uncouple the high-rate cell 60 from the low-power control circuit 52. In this regard, the circuitry 56A can include additional components/connections (not shown) for activating and deactivating the switch 70 in response to operational conditions described below.

The power source/circuitry configuration A provides a distinct advantage over prior art, single-cell designs. For example, during operation of the IMD 20 (FIG. 1), the power source 54A is, from time-to-time, required to deliver a high-current pulse or charge to the high-power output circuit 50 while maintaining a voltage high enough to continuously power the low-power control circuit 52. If the supply voltage drops below a certain value, the IMD 20 will cease operation. The power source/circuitry configuration A places the high-rate cell 60A and the lower-rate cell 62A in parallel to power the low-power control circuit 52 during periods when the high-power output circuit 50 is not activated. During a transient high power pulse, such as a defibrillation pulse, the switch 70 is opened to uncouple the high-rate cell 60A from the low-power control circuit 52. The lower-rate cell 62A remains electrically connected to the low-power control circuit 52. Thus, the lower-rate cell 62A continuously powers the low-power control circuit 52, regardless of any voltage drop experienced by the high-rate cell 60A. With the parallel configuration of the circuitry 56A, the high-rate cell 60A and the lower-rate cell 62A can be operated in combination for approximately the entire useful life of the respective cells 60A, 62A. Further, where desired, the cells 60A and/or 62A can be sized and shaped to satisfy certain volumetric or shape constraints presented by the IMD 20 (FIG. 1).

Figure 4:
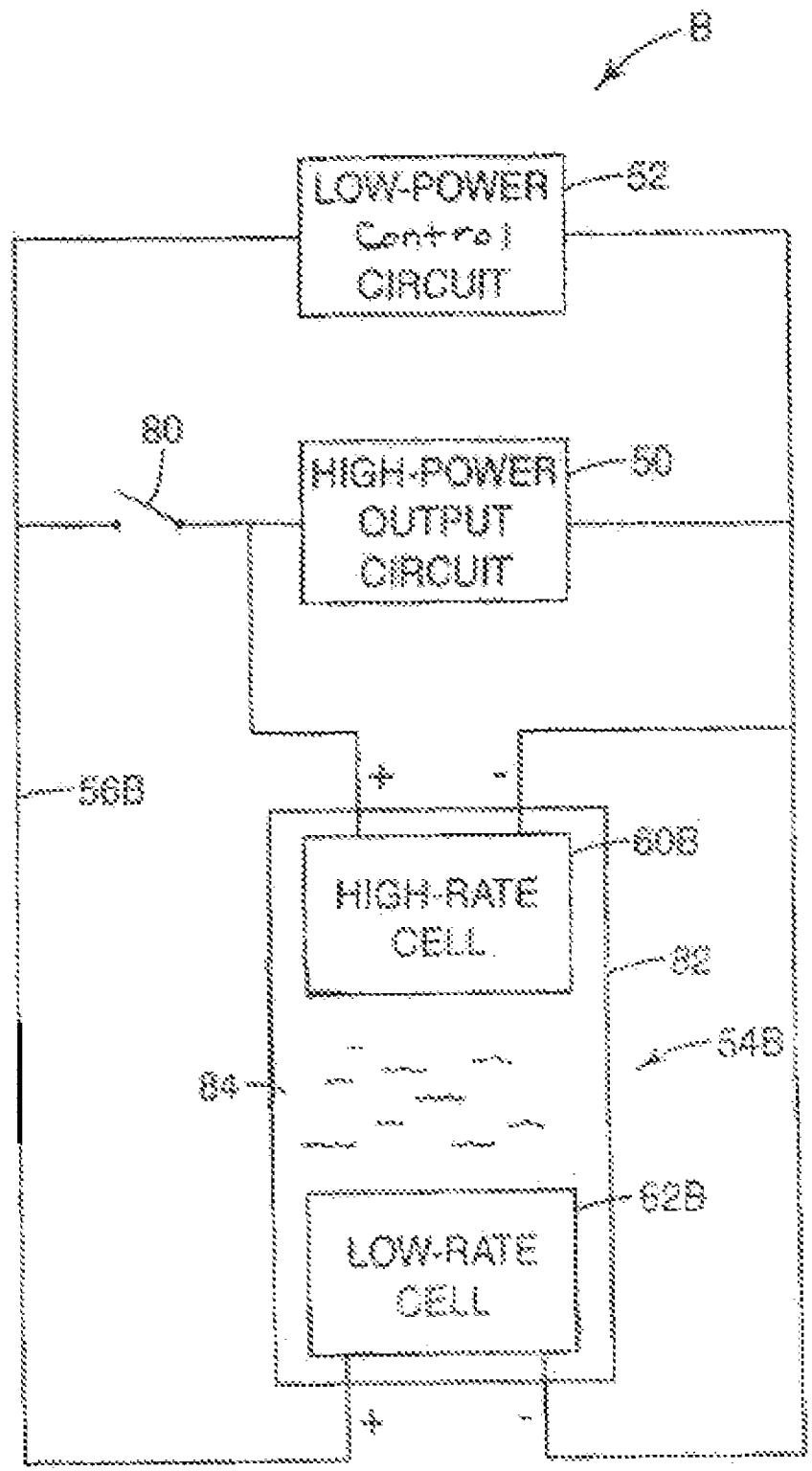
FIG. 4 is a simplified schematic diagram of a second embodiment power source in accordance with the present invention.

An alternative embodiment power source/circuitry configuration B is depicted schematically in FIG. 4. The power source/circuitry configuration B includes a power source 54B and circuitry 56B. The power source 54B includes a first, high-rate cell 60B and a second, lower-rate cell 62B. The circuitry 56B connects the high-rate cell 60B and the lower-rate cell 62B in parallel with the high-power output circuit 50 and the low-power control circuit 52, and includes a switch 80. The switch 80 is configured to selectively uncouple the high-rate cell 60B from the low-power control circuit 52, such that the circuitry 56B can include additional components/connections (not shown) for activating and deactivating the switch 80 in response to operational conditions described below.

The power source 54B is preferably a reservoir battery whereby both the high-rate cell 60B and the lower-rate cell 62B are maintained within a single case, shown generally at 82. In this regard, the high-rate cell 60B includes an anode/cathode combination that is electrochemically correlated (preferably identical) with an anode/cathode construction of the lower-rate cell 62B such that a common electrolyte 84 activates both cells 60B, 62B. For example, the high-rate cell 60B can be a high-rate Li/SVO, whereas the lower-rate cell 62B is a high-volumetric efficiency cell such as Li/SVO or a Li/$MnO_2$ cell with a pellet design. Alternatively, other constructions for the cells 60B, 62B, as previously described, are equally acceptable.

Connecting the cells 60B, 62B in parallel, via the circuitry 56B, to the high-power output circuit 50 and the low-power control circuit 52 allows for both cells 60B, 62B to power the low-power control circuit 52, thereby extending the useful life of the power source 54B. Further, as with the power source/circuitry configuration A (FIG. 3) previously described, the switch 80 ensures low-power control circuit 52 operation during transient high power pulses by the high-power output circuit 50. For example, when the high power output circuit 50 is prompted to deliver a high power pulse or charge, the circuitry 56B opens the switch 80 to uncouple the high-rate cell 60B from the low-power control circuit 52. The lower-rate cell 62B remains electrically connected, providing continuous, uninterrupted power to the low-power control circuit 52.

In addition, the lower-rate cell 62B can serve to recharge the high-rate cell 60B. More particularly, after the high-rate cell 60B is pulsed, the potential of the high-rate cell 60B will be lower than that of the lower-rate cell 62B. When the lower-rate cell 62B is re-connected to the high-rate cell 60B (via the switch 80), the lower-rate cell 62B will be discharged and the high-rate cell 60B correspondingly charged until they reach equal potentials. Electrons move from the anode of the lower-rate cell 62B to the anode of the high-rate cell 60B, and from the cathode of the high-rate cell 60B to the cathode of the lower-rate cell 62B. In one preferred embodiment, for recharging to occur, the high-rate cell 60B must possess at least some degree of rechargeability. That is to say, the high-rate cell 60B may not be rechargeable per the above description if discharged to a high degree. It has been found that configuring the high-rate cell 60B to exhibit a "micro-rechargeability" characteristic allows the small amount of capacity removed during operation of the high-power output circuit 50 (e.g., a therapy) to be replaced. It has further been found that a high-rate cell 60B including an SVO cathode exhibits this desired micro-rechargeability characteristic. Alternatively, other cathode materials may also be acceptable. Notably, this same recharging mechanism applies to the configuration A (FIG. 3) previously described.

As an additional advantage, the high-rate cell 60B can be sized (e.g., cell volume) to satisfy the requirements of the high-power output circuit 50, without specific concern for powering the low-power control circuit 52. As previously described, with prior art, single cell designs, cell volume is highly inefficient. The power source 54B overcomes this problem by minimizing the size of the high-rate cell 60B, and utilizing a more conveniently sized lower-rate cell 62B. In other words, the high-rate cell 60B can be a relatively simple shape that is conducive to coiled, serpentine, or other high-electrode area construction (but possibly with a lower volumetric energy density), whereas the lower-rate cell 62B can be of a shape that conforms and efficiently utilizes a desired volumetric shape of the IMD 20, such as a "D"-shaped pellet or bobbin cell with a relatively high volumetric energy density. The resulting power source 54B, by virtue of its unique, complex shape, utilizes the volume available in the IMD 20 and thus contributes to the IMD 20 having an optimal volume.

Figure 5A:
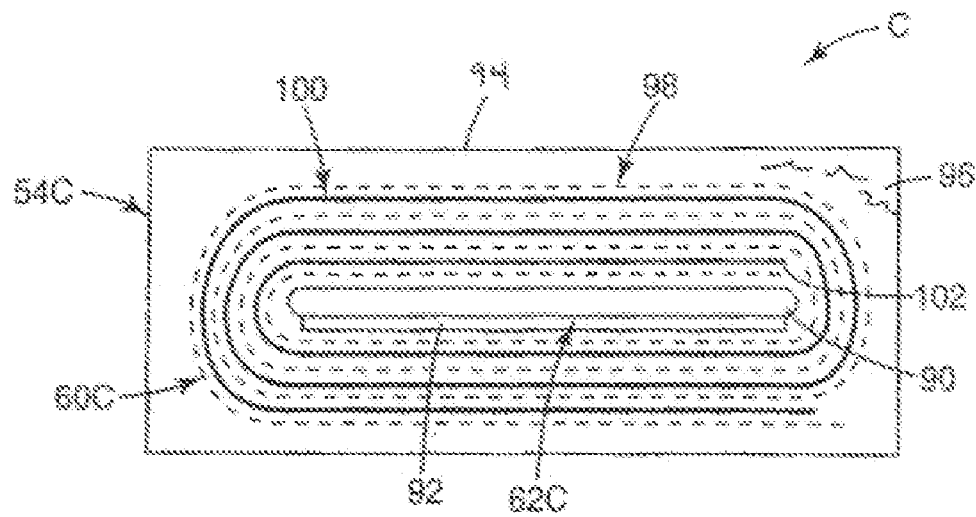
FIG. 5A is a cross-sectional view of a third alternative embodiment power source in accordance with the present invention.

Yet another alternative embodiment power source/circuitry configuration C is depicted in cross-section in FIG. 5A. More particularly, FIG. 5A shows a power source 54C including a high-rate cell 60C, a reservoir pellet 90, and a lithium body 92 that serve as a lower-rate cell 62C. The high-rate cell 60C, the pellet 90, and the lithium body 92 are disposed within a case 94 further containing an electrolyte 96. Although not shown in FIG. 5A, the high-rate cell 60C and the lower-rate cell 62C (comprised of the reservoir cathode pellet 90 and the lithium body 92) are connected in parallel to the high-power output circuit 50 (FIG. 2) and the low-power control circuit 52 (FIG. 2) by circuitry (not shown) that may or may not include a switch. Further, the lithium body 92 is approximately the same length and width as the cathode reservoir pellet 90.

Figure 5B:
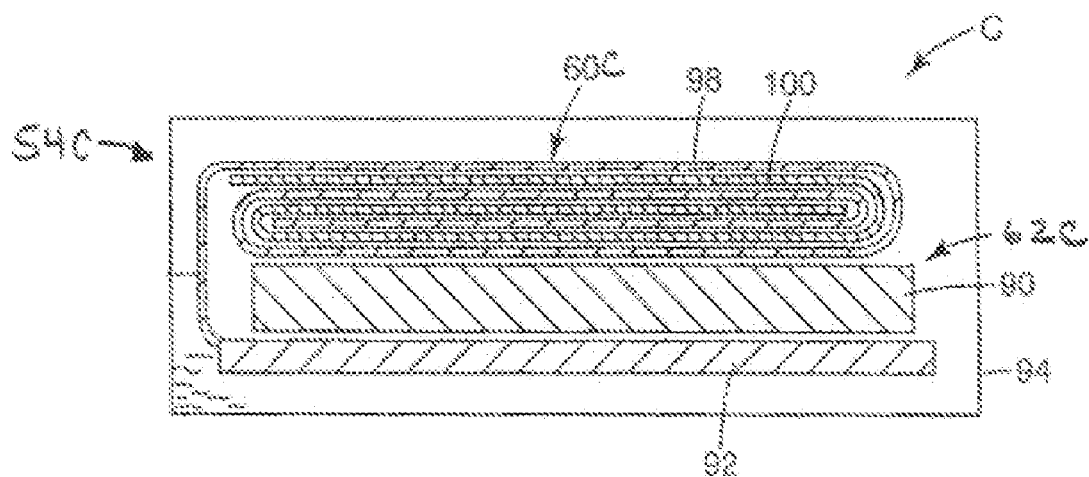
FIG. 5B is a cross-sectional view of a variation of the embodiment of FIG. 5A.

The high-rate cell 60C can assume a number of constructions, but preferably includes a coiled anode 98 and cathode 100. For example, the anode 98 is preferably a lithium material, whereas the cathode 100 is an appropriate metal-containing material (e.g., a metal oxide or metal sulfide), preferably SVO. Regardless, the anode 98 and the cathode 100 are preferably wound about the reservoir pellet 90. Alternatively, the reservoir pellet 90 and the lithium body 92 can be positioned outside of the winding of the high-rate cell 60C, as shown, for example, by the alternative embodiment of FIG. 5B.

Returning to FIG. 5A, the reservoir pellet 90 is of the same composition as the cathode 100. For example, in a preferred embodiment, the reservoir pellet 90 is a dense SVO or $MnO_2$ cathode pellet. Similarly, the lithium body 92 is of the same composition as the anode 98, and serves to balance the capability of the reservoir pellet 90. In this regard, the lithium body 92 need not be a separate element, but instead, an inner-most turn 102 of the anode 98 (i.e., surrounding the reservoir pellet 90) can be thickened (i.e., provided with additional lithium material).

The power source/circuitry configuration C provides the power source 54C with a higher energy density than a conventional parallel plate or coil configuration by utilizing the reservoir pellet 90 to charge the high-rate cell 60C without the difficulties of fabricating, coiling, or folding multiple thick electrodes.

During use, the high-rate cell 60C and the reservoir pellet 90 operate in parallel to power the low power control circuit 52 (FIG. 2). During a transient high-pulse operation, the high-rate cell 60C and the reservoir pellet 90 operate to power the high-power output circuit 50 (FIG. 2). Most of the power is delivered by the high-rate cell 60C due to its low internal resistance as compared to the lower-rate cell 62C (again, defined by the reservoir cathode pellet 90 and the lithium body 92). Following transient high-pulse operation, the lower-rate cell 62C preferably acts to recharge the high-rate cell 60C as previously described with respect to the power source 54B (FIG. 4). In particular, the reservoir pellet 90 serves as an auxiliary cathode, accepting electrons and lithium ions from the cathode 100 following the transient high-pulse operation. For example, where the reservoir pellet 90 is comprised of a material that is chemically compatible with the composition of the cathode 100 (e.g., SVO or $MnO_2$), as the high-rate cell 60C is discharged, the cathode 100 is charged or oxidized by the flow of electrons and lithium ions between the cathode 100 and the reservoir pellet 90. The resulting power source 54C has a higher average voltage, a higher volumetric energy density and an improved end of life voltage signal than a similar cell without the reservoir pellet 90. Further, the lithium body 92 balances the capacity of the reservoir pellet 90, thereby promoting recharging of the high-rate cell 60C following a transient high power pulse.

Figure 5C:
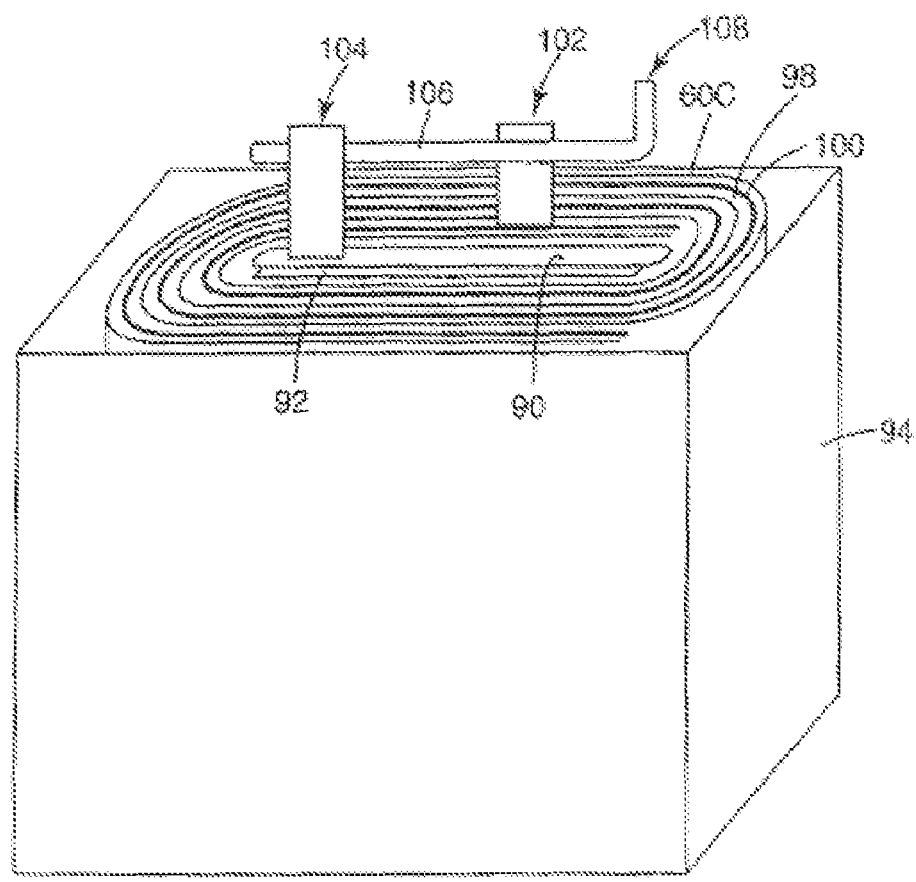
FIG. 5C is a perspective view of the power source of FIG. 5A including an internal, parallel connection.

In one more preferred embodiment of the power source 54C, the high-rate cell 60C and the lower-rate cell 62C (or the reservoir pellet 90) are connected in parallel, internal to the power source 54C itself. For example, FIG. 5C illustrates one interconnection technique associated with the configuration C of FIG. 5A. As a point of reference, a portion of the case 94 has been removed to better illustrate component interconnection. With this in mind, the power source 54C further includes a first conductive tab 102, a second conductive tab 104, and a connector 106. The first tab 102 is connected to and extends from the cathode 100 associated with the high-rate cell 60C. Conversely, the second tab 104 is connected to and extends from the reservoir (or cathode) pellet 90 forming the lower-rate cell 62C. Finally, the connector 106 interconnects the tabs 102, 104, and terminates in a feed through pin 108 otherwise extending outwardly from the battery case 94.

By internally connecting the cells 60C and 62C in parallel, only a single one of the feedthroughs 108 is required, thereby reducing the costs and complexities of other dual batter designs in which two or more feedthroughs are required. It will be understood that the construction of FIG. 5C necessitates that the cells 60C, 62C are not independently dischargeable, and a switch, such as the switch 80 of FIG. 4 is not available. However, the design promotes shape flexibility and volumetric efficiency. For example, one particular manufacturing concern associated with high-energy IMD power supplies is the requirement, due to known safety concerns, of a wound cell utilizing a thick cathode. Where a wound design is employed, the thick cathode material tends to crack in the corners and transmits stress through other components (such as a separator plate and/or lithium anodes). This may, in turn, lead to internal shorts. With the configuration of FIG. 5C, however, a substantial fraction of the energy supply is stored in the reservoir pellet 90 (or lower rate cell 62C), and the adjacent lithium body 92. The pellet 90 is not wound, and thus can be relatively thick without presenting the stress concerns associated with a wound cathode material. Because a substantial fraction of the energy is stored in the pellet 90, the cathode 100 material associated with the high-rate cell 60C can now be relatively thin, and thus more readily wound without experiencing stress-related defects. Further, by forming the reservoir pellet 90 to be relatively thick, a radius of the inner most winding associated with the high rate cell 60C is increased or greater than that found with conventional wound cells, again reducing winding-caused stress.

Figure 6:
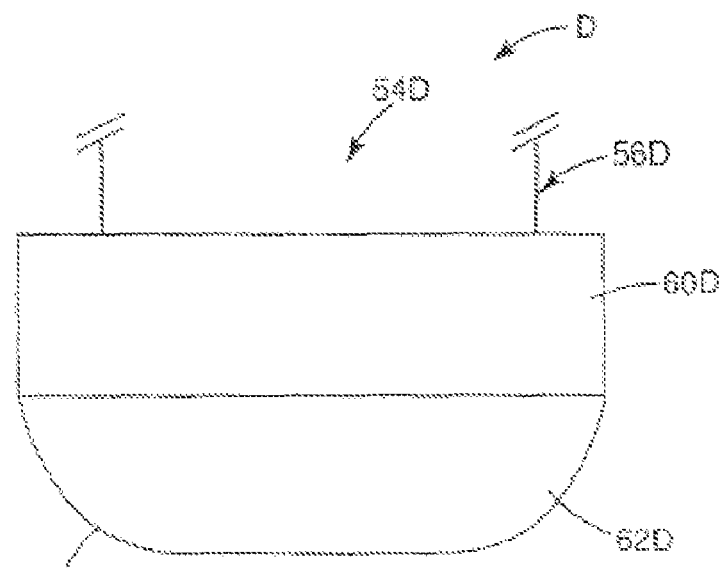
FIG. 6 is a top view of a fourth embodiment power source in accordance with the present invention.

Yet another alternative power source/circuitry configuration D having enhanced volumetric efficiency is depicted schematically in FIG. 6. The configuration D includes a power source 54D and circuitry 56D. The power source 54D includes a case 110 maintaining a high-rate cell 60D, a lower-rate cell 62D, and an electrolyte (not shown). The circuitry 56D connects the cells 60D, 62D in parallel with the high-power output circuit 50 (FIG. 2) and the low-power control circuit 52 (FIG. 2). Although illustrated schematically in FIG. 6, the high-rate cell 60D can assume any of the forms previously described and is preferably of a simple shape such that is conducive to assuming a coiled, serpentine, or other high-surface area electrode configuration. Conversely, the lower-rate cell 62D is a relatively low-surface area auxiliary electrode assuming an irregular shape, such as a D-shape, otherwise conforming and efficiently utilizing an available volume of the case 110. Once again, the lower-rate cell 62D can be comprised of any of the material(s) previously described, and can be a medium- or low-rate cell. Regardless, the resulting power source 54D, by virtue of its unique, complex shape, utilizes the volume available in the IMD 20 (FIG. 1) and thus contributes to an optimally sized device.

In operation, the power source 54D operates similar to previous embodiments, with the high-rate cell 60D and the lower-rate cell 62D operating in parallel to power the high-power output circuit 50 (FIG. 2) and the low-power control circuit 52 (FIG. 2). In this regard, the circuitry 56D associated with the power source 54D may include a switch (not shown) that uncouples the high-rate cell 60D from the low-power control circuit 52 during transient high power pulses. Operation of the lower-rate cell 62D in isolation from the high-rate cell 60D will continuously power the low-power control circuit 52 without concern for the voltage drop associated with the high-rate cell 60D. Further, when the power source 54D is subjected to a high-current pulse discharge, the high-rate cell 60D and the lower-rate cell 62D will equilibrate between pulses and thus stay at the same depth of discharge, with most of the capacity of the high-rate cell 60D being discharged at a higher voltage than would be observed without the lower-rate cell 62D connected in parallel.

Figure 7:
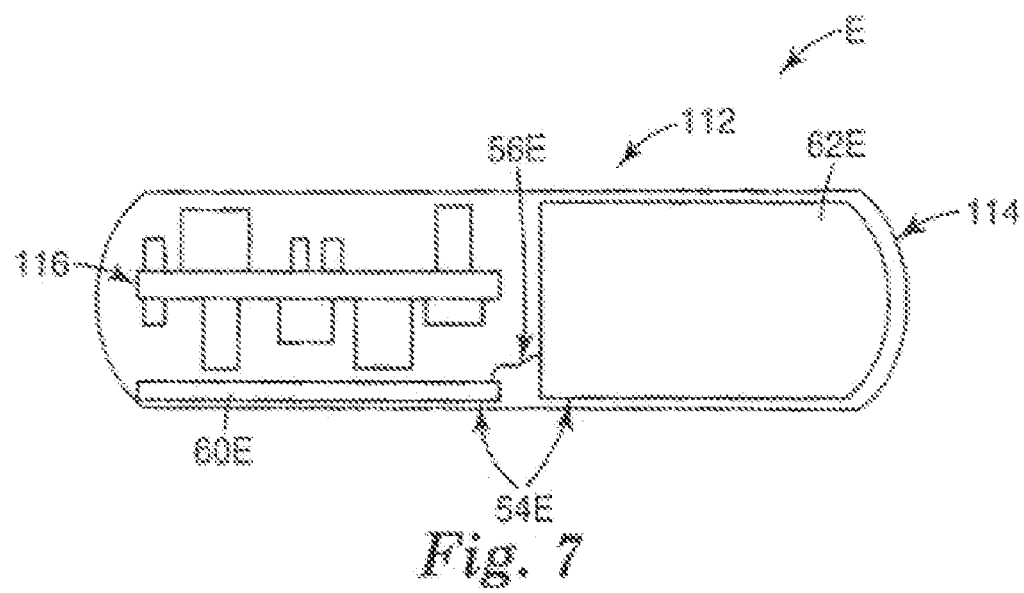
FIG. 7 is a cross-sectional view of an IMD incorporating a fifth embodiment power source.

Yet another, related alternative power source/circuitry configuration E having enhanced volumetric efficiency is depicted as part of an IMD 112 in FIG. 7. More particularly, the IMD 112 is shown as including a case 114, a circuit 116 (shown generally in FIG. 7), and the power source 54E. The power source 54E includes a high-rate cell 60E and a lower rate cell 62E. With the embodiment of FIG. 7, the cells 60E, 62E are separately formed (i.e., separate enclosures) and are connected in parallel via circuitry 56E. Notably, the circuitry 56E does not include a switch, and the cells 60E, 62E are not independently dischargeable.

Though illustrated schematically in FIG. 7, the high-rate rate cell 60E can assume any of the forms previously described and is preferably of a simple shape, conducive to assuming a coiled, serpentine, or other high-surface area electrode configuration. Conversely, the lower-rate cell 62E is a relatively low-surface area auxiliary electrode shaped to efficiently utilize an available volume of the case 114. In one preferred embodiment, the high-rate cell 60E is a thin film battery known in the art. In this regard, one preferred method of manufacturing a thin electrode is to prepare a slurry of electrode material in an appropriate solvent. This slurry is then applied to a thin foil substrate as the current collector. To this end, the most common method is to use a "knife over roller" approach, whereby the slurry is applied to a moving web (e.g., the metal foil) using a knife edge to control thickness (i.e., a Doctor blade). The solvent is then evaporated leaving a thin film of cathode material. Alternatively, other known thin electrode manufacturing techniques are equally acceptable.

By forming the high rate cell 60E as a thin film battery, the power source 54E is characterized by an improved volumetric efficiency. Further, especially where the IMD 112 is an ICD, the power source 54E presents improved scaleability. As a point of reference, ICD batteries are typically built with maximum safe power capability (i.e., maximum safe electrode surface area). Thus, changing the size of a "standard" ICD battery in one dimension while maintaining a specific surface area typically imposes more geometric constraints than can be satisfied. As a result, for differently sized ICD applications, the "standard" ICD battery must often be changed in two dimensions, and therefore is not scaleable. The dual cell design of FIG. 7 overcomes this problem. In particular, by forming the high-rate cell 60E as a thin electrode allows the high-rate cell 60E to be located underneath the circuit 116. Conversely, the lower rate cell (preferably a medium-rate cell) 62E is constructed to have the same thickness as the internal dimensions of the case 114 (i.e., the same thickness as the circuits 116 and the high-rate cell 60E). As shown in FIG. 7, then, the lower rate cell 62E is positioned adjacent the circuit 116/high-rate cell 60E stack. The high-energy capacitors (not shown) of the ICD 112 are located on the other side of the lower-rate cell 62E and match the medium rate cell 62E in thickness. For a differently sized ICD, the lower rate cells 62E can be scaled in one dimension to provide the energy needs for a particular application. However, the circuit 116, the high-rate cell 60E, the capacitors, and any device connector blocks (not shown) are all fixed components that do not vary. Thus, the configuration of FIG. 7 meets desired scaleability criteria.

Figure 8:
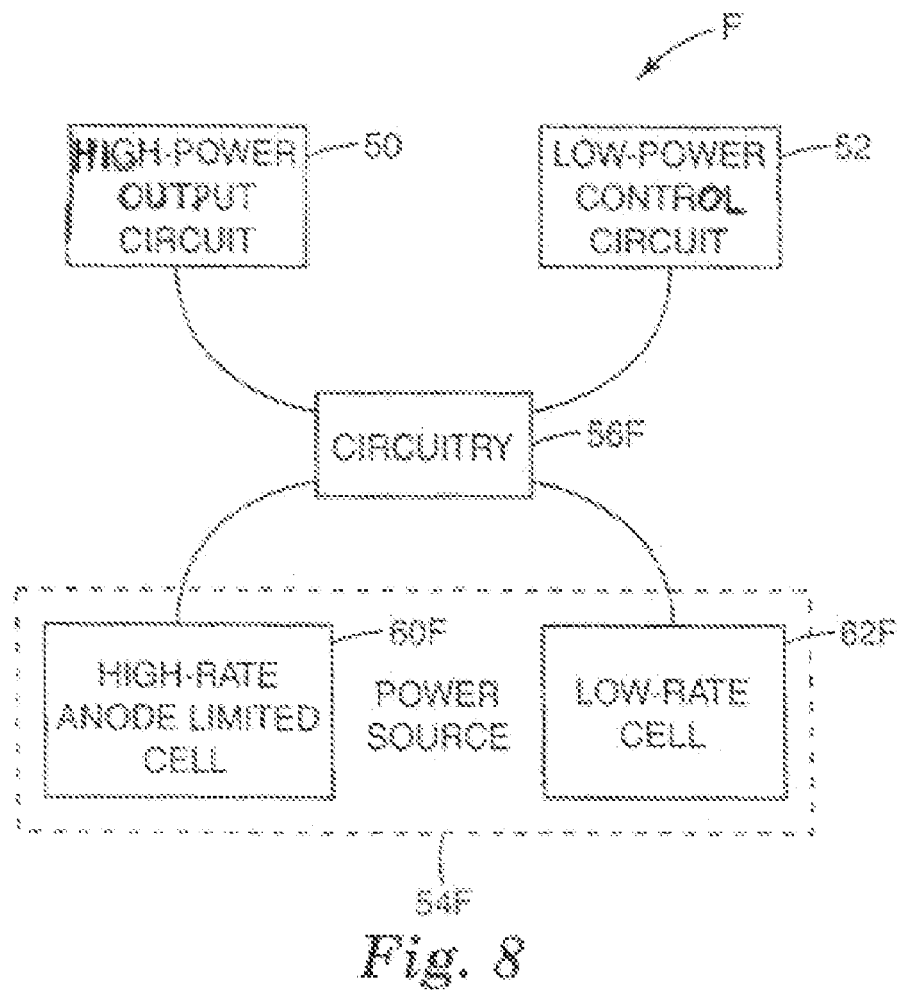
FIG. 8 is a simplified schematic diagram of a sixth embodiment power source.

Another alternative embodiment power source/circuitry configuration F is depicted schematically in FIG. 8. The configuration F includes a power source 54F and associated circuitry 56F. Once again, the power source 54F includes a first, high-rate cell 60F and a second, lower-rate cell 62F. The circuitry 56F connects the high-rate cell 60F and the lower-rate cell 62F to the high-power output circuit 50 and the low-power control circuit 52. Unlike previous embodiments, the circuitry 56F need not necessarily connect the cells 60F, 62F in parallel. Further, while the lower-rate cell 62F is highly similar to previously described embodiments, the high-rate cell 60F is preferably an anode limited cell as described below.

In particular, for the configuration F, the high-rate cell 60F includes a solid cathode, liquid organic electrolyte and a lithium anode for delivering high current pulses. The cell 60F further includes a casing (not shown) containing the cell components and the cathode structure generally wound in a plurality of turns, with the lithium anode interposed between the turns of the cathode winding. The casing also contains a non-aqueous liquid organic electrolyte preferably comprising a combination of lithium salt and an organic solvent operatively contacting the anode and the cathode. An electrical connection is provided to the anode and an electrical connection is provided to the cathode. The cathode includes an active material such as SVO or $MnO_2$.

With the above-construction, the high-rate cell 60F is a volumetrically constrained system. The amounts of each component that goes into the cell 60F (cathode, anode, separator, current collectors, electrolytes, etc.) cannot exceed the available volume of the battery case. In addition, the appropriate amount of some components depends upon the amount of other components that are used. These components must be "balanced" to provide discharge to the extent desired.

For example, in a cathode limited Li/SVO battery such as is used in a defibrillator application, the capacity ($Q_+$) of the cathode must not exceed the capacity ($Q_-$) of the anode. The volume occupied by the other battery components also depends on the cathode capacity ($Q_+$) as reflected by the amount of cathode material in the battery. All of the battery components must be adjusted for a given battery volume.

Conventionally balanced lithium anode cells used with ICDs are balanced with sufficient lithium and electrolyte to discharge the cathode to completion. However, conventionally balanced cells have impedances that increase with time and depth-of-discharge. The power capability of these cells is limited by electrode area constraints imposed for safety reasons. Historically, it has been possible to use nearly the total capacity of the battery while maintaining adequate power (i.e., acceptable charge times). However, over time, conventionally balanced high-rate cells exhibit increased charge times due to increased cell impedance. When the cell can no longer satisfy charge time requirements, the ICD (or other IMD) must be replaced. To this end, industry standards have implemented more rigorous charge time requirements. Hence, it has become increasingly difficult to use the entire cell capacity before charge time failure.

Figure 9:
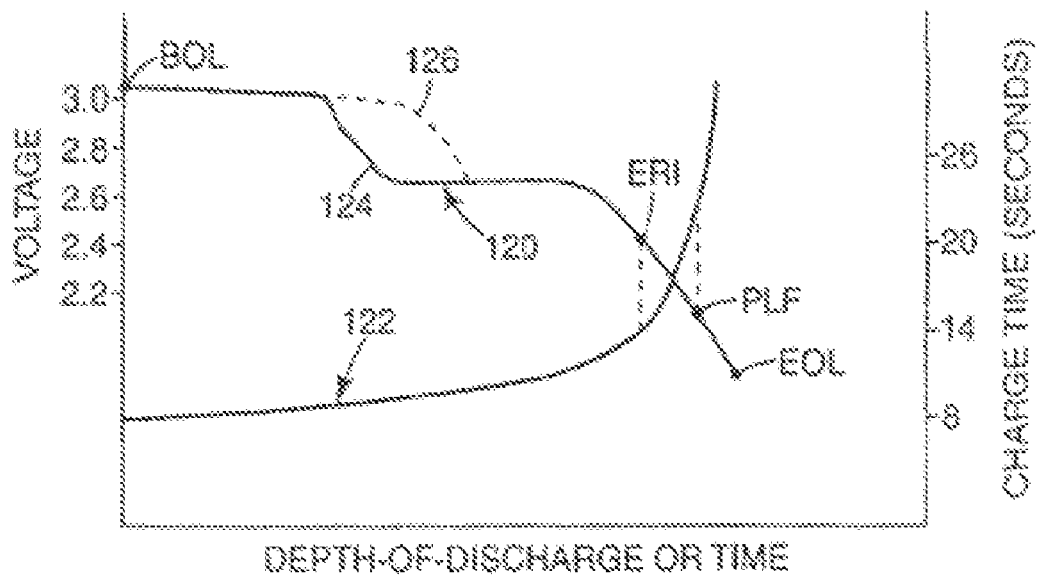
FIG. 9 is a graph showing a discharge curve for a conventionally balanced battery.

One example of the above-described concern experienced by a Li/SVO type cell is illustrated graphically in FIG. 9. In particular, a conventional, Li/SVO high-rate cell design experiences a decrease in voltage over time as shown by curve 120. In addition, due to the increase in internal resistance over time results in an increasing capacitor charge time, as represented by the curve 122. As a point of reference, the curves 120, 122 extend from a beginning of life (BOL) point to an end of life (EOL) point. Just prior to EOL, manufacturers typically delineate a potential loss of function (indicated at "PLF" in FIG. 9) for the power source with respect to a particular IMD application. PLF is determined by circuit performance requirements of the IMD. For the example of FIG. 9, according to manufacturer standards, the conventionally balanced cell will experience a potential loss of function (PLF) at approximately 2.20 volts. To ensure that the IMD is explanted and replaced prior to PLF, industry standards require the IMD to provide an elective replacement indicator (ERI) to the user. The ERI is normally designated by the manufacturer with reference to the voltage curve 120 just prior to the PLF. For example, a manufacturer's standards may require that the IMD continue to operate for three months after ERI. With this standard in mind, the manufacturer works backwards from the PLF to select an ERI value that satisfies the so-selected standard. With reference to the example of FIG. 9, a common ERI value is 2.45 volts.

With the above definitions in mind, FIG. 9 illustrates graphically that the charge time curve 122 is dependent upon depth-of-discharge or time, increasing from BOL to both ERI and PLF. Due to this time dependence, and as a point of reference, the charge time for a typical high-rate cell useful with an IMD is approximately 8 seconds at BOL, 14 seconds at ERI, and 25 seconds at PLF. As IMD performance requirements continue to evolve, it is highly likely that charge times in excess of 16 seconds may no longer be acceptable. In other words, future industry requirements may require a PLF value of 16 seconds (and thus a correspondingly decreased ERI value). While an IMD incorporating a lithium-based high-rate cell can be programmed to provide an earlier ERI signal (relative to the charge time curve 120), due to the dependence upon depth-of-discharge or time, only a small portion of the battery's capacity will be used at this reduced ERI level. For example, at ERI corresponding with a charge time of 12 seconds, approximately 40% of a conventional cell's capacity has been used. Obviously this low efficiency is highly undesirable.

To overcome the time-dependent characteristics associated with previous lithium-based high-rate cells, the power source 54F (FIG. 8) forms the high-rate cell 60F (FIG. 8) to be anode limited. In particular, the high-rate cell 60F is preferably a lithium limited cell as described, for example, in U.S. Pat. No. 5,458,997, the teachings of which are incorporated herein by reference. Generally speaking, available lithium-based high-rate cells, such as Li/SVO, Li/$MnO_2$, etc., are re-balanced such that the cell contains sufficient lithium and electrolyte to be discharged only to a first voltage plateau (labeled as 124 in FIG. 9). The volume made available by using less lithium and electrolyte allows more room for cathode material, thereby extending the first voltage plateau as shown by the dotted line 126. With this configuration, the lithium anode is depleted prior to cathode depletion, thereby prohibiting the formation of gas. In addition, the lithium limited design generates minimal impedance over a majority of the battery's life. In one preferred embodiment, the lithium limited, high-rate cell 60F is a SVO/$CF_x$ hybrid cathode design, where x is in the range of 0.9-1.1.

Figure 10:
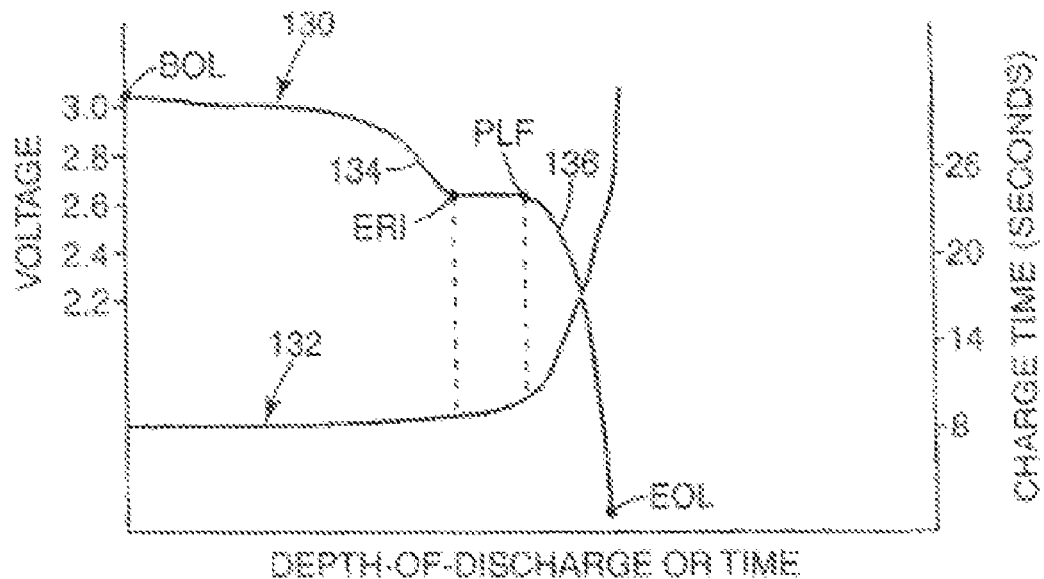
FIG. 10 is a graph showing a discharge curve for an anode limited battery for use with the power source of FIG. 8.

As illustrated graphically in FIG. 10, the lithium limited high-rate cell 60F (FIG. 8) exhibits charge time characteristics that have little dependence upon depth-of-discharge or time. As a point of reference, FIG. 10 depicts a voltage curve 130 and a charge time curve 132. As compared to the conventionally balanced cell performance characteristics illustrated in FIG. 9, the voltage curve 130 of the lithium limited high-rate cell 60F has an extended first voltage plateau 134, and a rapid voltage decrease after the second voltage plateau 136. Importantly, however, prior to a second voltage plateau 136, the charge time curve 132 increases only slightly, if at all, with increased depth-of-discharge and/or time. Effectively, then, the lithium limited high-rate cell 60E is characterized by a rate capability that exhibits minimal dependence on time or depth-of-discharge throughout a majority of the battery's life. With this characteristic in mind, an IMD incorporating the power source 54F (FIG. 8) including the high-rate cell 60F can be programmed to establish the PLF and ERI values shown in FIG. 10.

By way of example, and in accordance with one preferred embodiment, the PLF is established at approximately 2.6 volts and the ERI at 2.65 volts. At these values, the rate capability or charge time curve 132 exhibits minimal dependence upon depth-of-discharge and time. For example, the BOL charge time is approximately 8 seconds, the ERI charge time is approximately 10 seconds, and the PLF charge time is approximately 16 seconds. Following the second voltage plateau 136, the charge time rapidly increases to EOL. However, unlike conventionally balanced cells, the ERI and PLF of the anode limited high-rate cell 60F are relatively close to the EOL (relative to an overall length of the voltage curve 130). Thus, unlike conventionally balanced high-rate cells, the anode limited high-rate cell 60F allows for selection of an ERI value at which rate capability and charge time has minimal dependence upon depth-of-discharge or time, and results in a large portion of the cell's 60F capability being utilized. More particularly, the ERI of the high-rate cell 60F is selected such that at least 40 percent of the cathode is consumed; preferably at least 50 percent; more preferably at least 60 percent; most preferably at least 75 percent.

As previously described, with embodiment F (FIG. 8), the high-rate cell 60F and the lower-rate cell 62F need not necessarily be connected in parallel. However, with parallel wiring, the lower-rate cell 62F will effectively recharge the high-rate cell 60F following a transient high power pulse, according to the recharging mechanism previously described. Further, with the parallel configuration, it is preferred that the lower-rate cell 62F be designed to have a higher voltage (beyond BOL) than the high-rate cell 60F such that as the cells 60F, 62F are discharged, the high-rate cell 62F will remain nearer its BOL voltage and rate capability through more of the cell's 60F useful life. In an even further preferred embodiment of configuration F employing a parallel construction, the high-rate cell 60F is a lithium-limited SVO cell and the lower-rate cell 62F is a $SVO/CF_x$ hybrid cathode low-rate cell. This construction provides both of the cells with similar BOL voltages, similar depletion voltages (e.g., greater than 90% depletion at PLF), and the lower-rate cell 62F will have a higher voltage (beyond BOL) than the high-rate cell 60F.

The IMD with dual cell power source of the present invention provides a marked improvement over previous designs. In one embodiment, by connecting a first, high-rate cell and a second, lower-rate cell in parallel to a control circuit and an output circuit, and including a switch to selectively uncouple the high-rate cell and the control circuit, the IMD will efficiently utilize the capacity in both cells independent of charge conditions. Regardless of whether the switch is included, the preferred parallel connection can facilitate the lower-rate cell recharging the high-rate cell following a transient high power pulse depending upon a construction of the high-rate cell. In another alternative embodiment, the dual cells are provided as a single reservoir. In yet another alternative embodiment, the high-rate cell has an anode-limited construction and exhibits a charge time characteristic that has minimal dependence on time or depth-of-discharge. With this configuration, a majority of the high-rate cell's capacity is utilized while satisfying rigorous charge time requirements.

Figure 11:
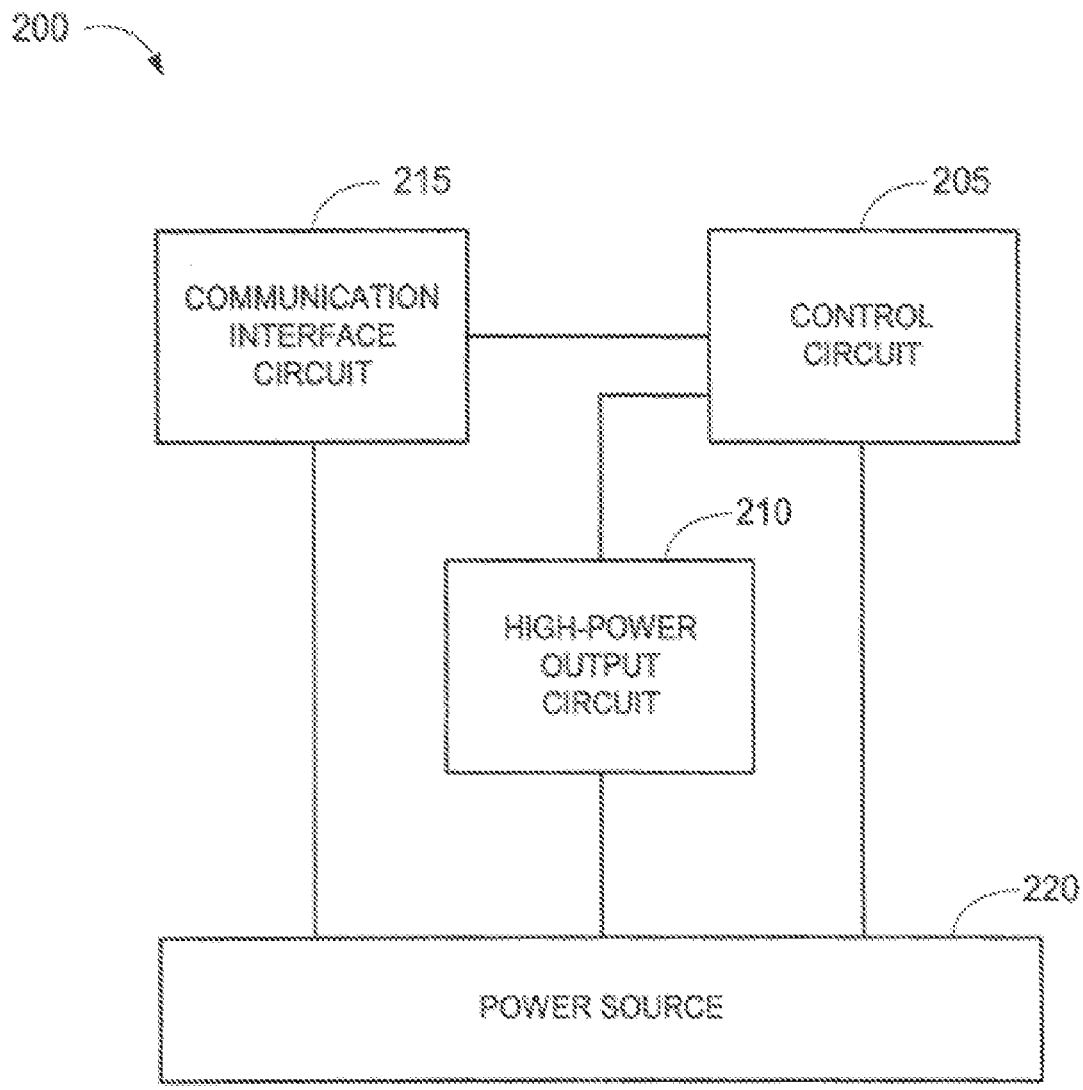
FIG. 11 is a simplified block diagram of an implantable medical device (IMD) incorporating a power source in accordance with another embodiment of the present invention.

FIG. 11 illustrates an implantable medical device (IMD) 200 in accordance with another embodiment of the present invention. The IMD 200 according to this embodiment may be provided in the form of a pacemaker, cardioverter, defibrillator, neural stimulator, or drug administering device. It will be appreciated, however, that the IMD 200 may take the form of various other implantable medical devices, and, thus, need not necessarily be limited to the aforementioned examples. For purposes of illustration, however, the IMD 200 will be described in the configuration of an implantable cardiac defibrillator (ICD).

According to the illustrated embodiment, the IMD 200 comprises a control circuit 205 that controls the overall operation of the IMD 200. The control circuit 205 may be configured to monitor physiological data via one or more electrodes disposed within the patient's body, which are coupled to the IMD 200 via electrical leads. For example, the control circuit 205 may monitor cardiological activity via one or more electrodes implanted within the patient's heart. The control circuit 205 may collect and process the physiological data received via the implanted electrodes. Depending on the physiological data received at the IMD 200 via the implanted electrodes, the control circuit 205 may further be configured to deliver a therapy to a part of the patient's body. In accordance with the exemplary embodiment, the therapy may be provided in the form of a therapeutic electric pulse that is delivered to the patient's heart via the one or more electrodes implanted within the heart.

Figure 11A:
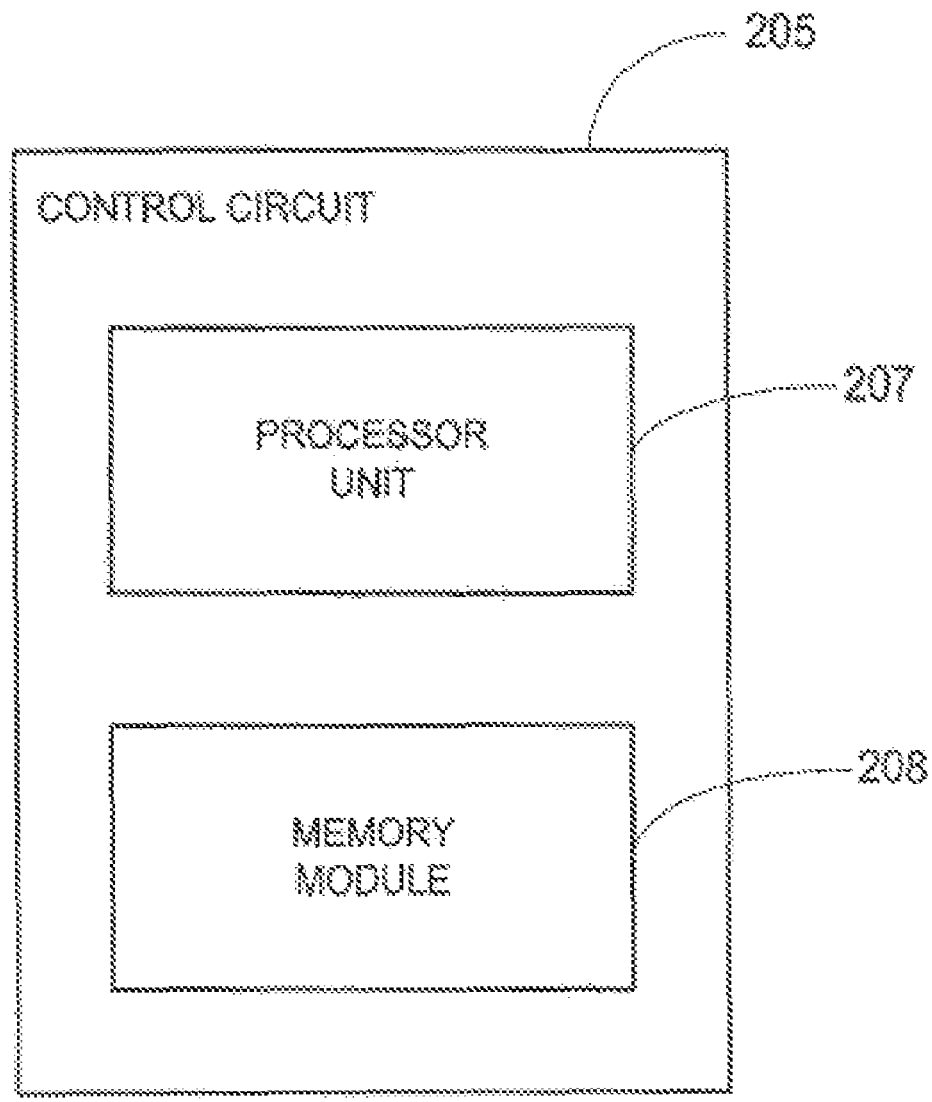
FIG. 11A is a more detailed representation of a control circuit of the IMD of FIG. 11.

In accordance with one embodiment of the present invention, the control circuit 205 is provided in the form of a processor unit 207, as shown in FIG. 11A, to control the overall operation thereof. In one embodiment, the processor unit 207 may, for example, take the form of a microprocessor, a microcontroller, or a digital signal processor. The control circuit 205 may further include a memory module 208 for storing the physiological data that is received by the one or more electrodes implanted within the patient's body. The memory module 208 may also store software firmware, and/or microcade that executes on the processor unit 207 for controlling the IMD 200.

Referring again to FIG. 11, the IMD 200 may further include a high power output circuit 210 for delivering an electrical pulse therapy, such as a defibrillation or cardioversion/defibrillation pulse in accordance with the exemplary embodiment. The high power output circuit 210 may be provided in the form of a capacitor (not shown) for generating a high output electronic pulse that is delivered to the patient's heart via the one or more electrodes that are implanted therein. According to the illustrated embodiment, the high power output circuit 210 may receive a control signal from the control circuit 205 to deliver the high output electric shock in response to the analysis of the physiological data (i.e., electric cardiac signals) received via the one or more electrodes implanted within the patient's heart.

In accordance with the illustrated embodiment, the IMD 200 is further provided with a communication interface circuit 215, which may provide communication capabilities for the IMD 200 to communicate with an external data processing device. The data processing device may be configured to monitor and/or analyze the physiological data that is collected and subsequently transmitted by the IMD 200. It will be appreciated, however, that the communication interface circuit 215 may also be configured to communicate with various other devices that are external to the patient's body without departing from the spirit and scope of the present invention. In an alternative embodiment, the communication interface circuit 215 may communicate with a transmitting device (not shown) that is external to the IMD 200, but within the patient's body. This transmitting device may then communicate with an external data processing unit.

According to the illustrated embodiment, the communication interface circuit 215 is configured to communicate physiological data obtained by the control circuit 205 from the one or more electrodes implanted within the patient's body. The communication interface circuit 215 may also be configured to receive data that is generated by another device externally from the IMD 200 that is to be processed by the control circuit 205. According to the illustrated embodiment, the communication interface circuit 215 communicates data with the external device via wireless communication.

In accordance with the illustrated embodiment, the IMD 200 is further configured with a power source 220 to provide electrical power to the control circuit 205, high power output circuit 210 and the communication interface circuit 215. The power source 220 inherently plays a significant role in the operation of the IMD 200 since the IMD may enter of limited function mode as the battery approaches end-of-life. As such, the IMD may not be capable of delivering an appropriate therapy to the patient, thereby compromising the patient's health. Moreover, because the IMD 200 is implanted within the patient's body, battery accessibility usually requires a surgical procedure. Accordingly, if the power source 220 fails, the patient's health may be placed in jeopardy until such procedure is performed.

Figure 12:
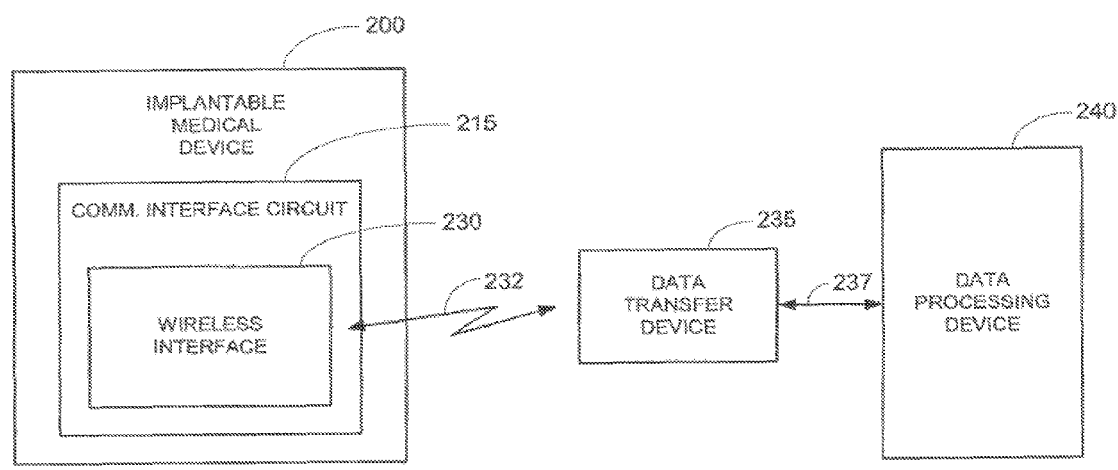
FIG. 12 illustrates the communication capabilities of the IMD of FIG. 11 with an external data processing device.

Turning now to FIG. 12, the communication capabilities of the IMD 200 with an external device is shown in accordance with one embodiment of the present invention. The communication interface circuit 215 of the IMD 200 is configured with a wireless interface 230 for communicating through a wireless communication medium 232 to a data processing device 240 via a data transfer device 235. In accordance with the illustrated embodiment, the wireless interface 230 may take the form of a radio frequency (RF) transceiver that transmits and receives radio frequency signals with the data transfer device 235, which is also configured with an RF transceiver. It will be appreciated, however, that other forms of communication protocols may be utilized between the wireless interface 230 of the IMD 200 and the data transfer device 235 either in lieu of or in addition to radio frequency communication without departing from the spirit and scope of the present invention. For example, the communication protocol utilized between the wireless interface 230 and the data transfer device 235 may include ultrasound communication, among other types of communication.

According to the illustrated embodiment, the data transfer device 235 may be provided in the form of a hand-held device that may be proximately placed to the implantable medical device 200 implanted within the patient's body. In this embodiment, the data transfer device 235 is coupled to the data processing device 240 via a wired link 237. It will be appreciated, however, that the data transfer device 235 may alternatively communicate with the data processing device 240 via a wireless communication medium. For example, the wireless communication medium between the data transfer device 235 and the data processing device 240 may be an RF communication medium or an infrared (IR) communication medium. Alternatively, in one embodiment, data transfer device 235 is eliminated, with the data transfer occurring directly between wireless interface 230 and data processing device 240.

It will further be appreciated that the power level of the communication signals between the communication interface circuit 215 of the IMD 200 and the data transfer device 235 may vary as well. For example, low power RF communication may be used between the IMD 200 and the data transfer device 235 such that it may have to be placed within close proximity to the IMD 200. Alternatively, a higher transmission power level may be used over the RF communication medium 232 such that close physical proximity of the data transfer device 235 and the IMD 200 is not necessary. Of course, it will be appreciated that the higher the transmission power level that is used over the RF communication medium 232, the higher the drain on the power source 220 of the IMD 200.

As previously mentioned, the physiological data is collected by the control circuit 205 of the IMD 200 via the one or more implanted electrodes within the patient's body. In one embodiment, the physiological data may take the form of electrical cardiac signals from electrodes implanted within the patient's heart, and recorded within the memory module 208 of the IMD 200 in the form of an electrocardiogram, for example. The physiological data may subsequently be retrieved from the memory module 208 and transferred to the communication interface circuit 215 for wireless transmission to the data transfer device 235 for monitoring and/or processing by the data processing device 240. In an alternative embodiment, the physiological data may be obtained by the control circuit 205 and transferred to the communication interface circuit 215 for transmission to the data transfer device 235 on a real-time basis as the data is sensed by the one or more implanted electrodes within the patient's body. In addition to the transmission of physiological data to the data processing device 240 via the data transfer device 235, the communication interface circuit 215 may also transmit data relating to the performance of the IMD 200. The performance data may include, for example, the effectiveness of a previously delivered therapy from the IMD 200 to the patient's body.

In accordance with one embodiment of the present invention, the data processing device 240 is provided in the form of a programmer or other computer. The data processing device 240 may be used to monitor and/or analyze the physiological data and/or performance data transmitted from the IMD 200 via the communication interface circuit 215. The data processing device 240 may also determine the efficiency of the therapy that is delivered by the IMD 200 based upon the physiological data and performance data collected. For example, the data processing device 240 may be used to determine whether the therapy delivered to the patient was of a proper energy intensity.

Based upon the analysis performed by the data processing device 240 using the physiological and performance data that was received by the IMD 200, the data processing device 240 may also be configured to transmit programming data to the IMD 200 via the data transfer device 235 to adjust various settings of the IMD 200. For example, if it is determined by the data processing device 240 that the IMD 200 is delivering a higher intensity of an electric pulse therapy signal than is necessary (based upon the physiological data collected, for example), the programming data transmitted to the IMD 200 may reduce the intensity of the electric therapy signal delivered to the patient's body.

Typically, the communication interface circuit 215 of the IMD 200 requires relatively high current pulses, thus resulting in a relatively higher drain from the power source 220. If a substantial amount of data is communicated between the communication interface circuit 215 and the data transfer device 235, it may create a significant drain on the power source 220 because of the high current pulses and the amount of time the communication interface circuit 215 is transmitting data. Additionally, as the amount of data communicated between the IMD 200 and the data transfer device 235 increases, the burden placed on the power source 220 is also increased, thereby decreasing the life of the power source 220 within the IMD 200.

Figure 13:
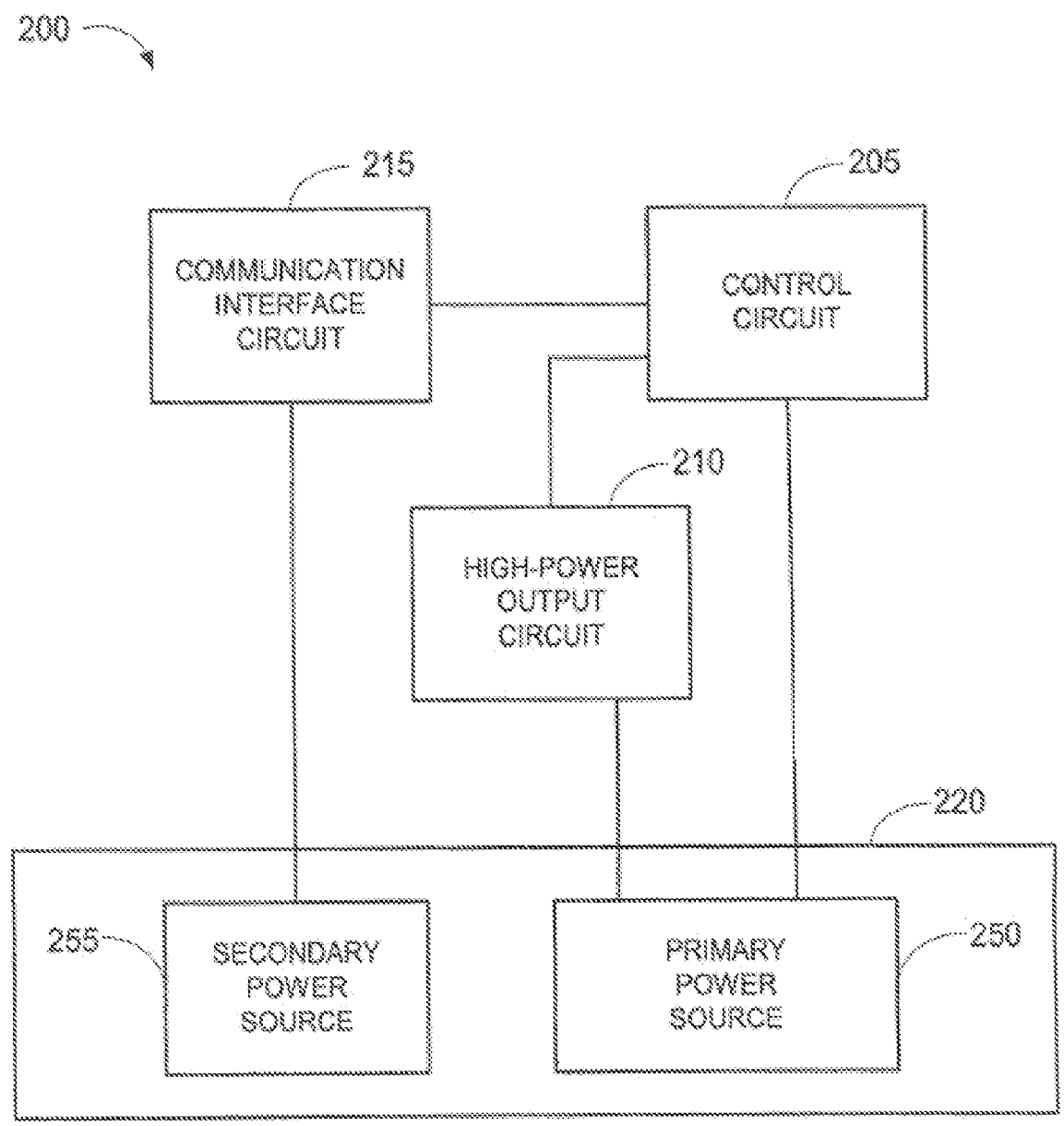
FIG. 13 is a more detailed representation of the power source of the IMD of FIG. 11 in accordance with one embodiment of the present invention.

Turning now to FIG. 13, a more detailed representation of the power source 220 is provided according to one embodiment of the present invention. The power source 220 comprises a primary power source 250 and a secondary power source 255. The primary power source 250 is used to power the control circuit 205 of the IMD 200, as well as the high-output power circuit 210. In accordance with one embodiment of the present invention, the primary power source 250 takes the form of a lithium/$CF_x$-CSVO battery. It will be appreciated, however, that the primary power source 250 may take the form of various other battery types, which may include Li/CSVO, Li/$CF_x$, Li/$MnO_2$, Li/I2, Li/$SOCl_2$, or other similar type chemistries.

In accordance with the illustrated embodiment, the secondary power source 255 provides power to the communication interface circuit 215 to alleviate any additional burden that the communication interface circuit 215 would have placed on the primary power source 250. In accordance with one embodiment, the secondary power source 255 is provided in the form of a rechargeable battery. The secondary power source 255 may comprise a lithium-ion battery with either a liquid or polymer electrolyte. It will be appreciated, however, that the secondary power source 255 may also take the form of other battery types, such as nickel/metal hydride or other similar type chemistries without departing from the spirit and scope of the present invention. According to the illustrated embodiment, the secondary power source 255 may be recharged via a transcutaneous magnetic induction process, as is well established in the art.

In accordance with one embodiment, the secondary power source 255 powers only the communication interface circuit 215, thereby relieving the burden of additional power requirements that the communication interface circuit 215 would require from the primary power source 250. Thus, in this embodiment, the secondary power source 255 is a dedicated power source for the communication interface circuit 215. Accordingly, the primary power source 250 needs to provide power only to the essential "life-support" operating circuitry of the control circuit 205 and the high-output power circuit 210 without the need to provide power to support the IMD 200's communication requirements (i.e., through the communication interface circuit 215), thereby conserving the power and life of the primary power source 250. The primary power source may take the form of any of the dual-cell embodiments discussed above. Alternatively, the primary power source may be a conventional, single-cell design.

In the illustrated embodiment of FIG. 13, the power sources 250 and 255 may operate independently of each another. Thus, in one embodiment, if one of the power sources 250, 255 fails, the other power source 250, 255 continues to power its respective circuit(s).

Figure 14:
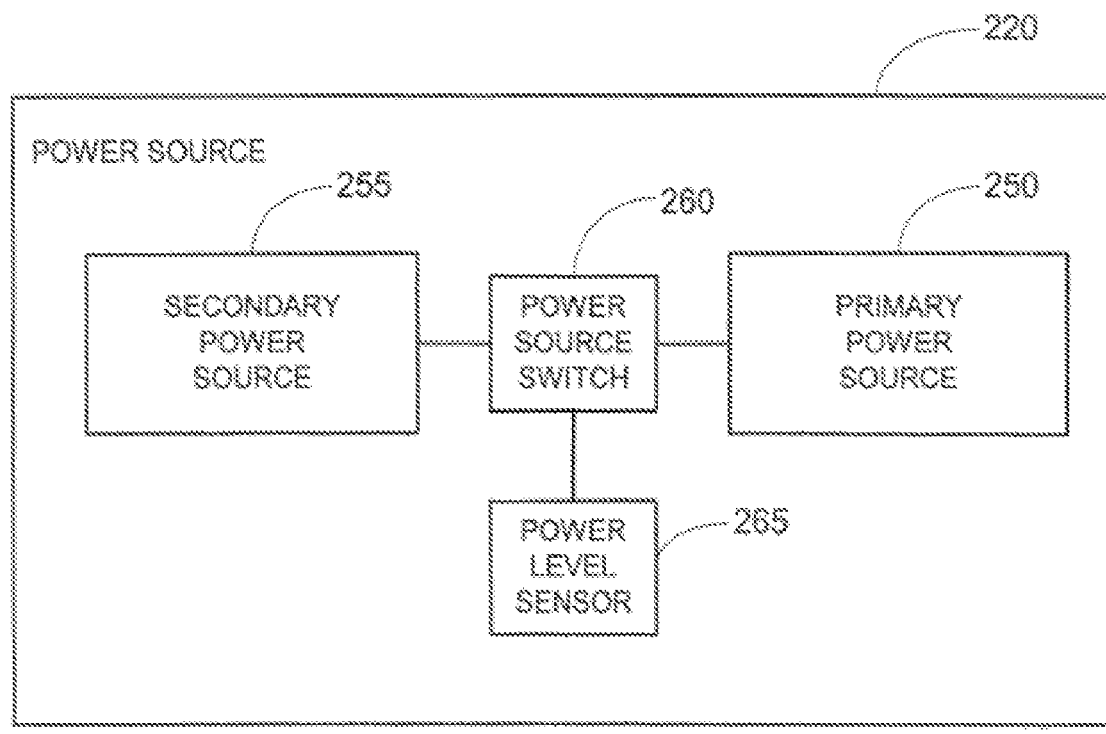
FIG. 14 illustrates another more detailed representation of the power source of the IMD of FIG. 13 according to another embodiment of the present invention.

Turning now to FIG. 14, the power source 220 is shown in accordance with another embodiment of the present invention. In this particular embodiment, the primary power source 250 and the secondary power source 255 are coupled to a power source switch 260, which is capable of switching connections to provide power to the various components of the IMD 200. As mentioned with the configuration provided in FIG. 13, the primary power source 250 ordinarily provides power only to the control circuit 205 and the high output power circuit 210 of the IMD 200. The secondary power source 255, on the other hand, ordinarily provides power only to the communication interface circuit 215. In accordance with the illustrated embodiment of FIG. 14, the power source switch 260 is configured to switch connections of the primary power source 250 and/or the secondary power source 255 depending on whether or not the power sources 250, 255 are depleted of their power.

In accordance with one embodiment, the switch 260 is coupled to a power level sensor 265, which is configured to determine the remaining power level of the primary power source 250 and/or secondary power source 255. The power level sensor 265 may be further configured to determine whether the remaining power level of the primary and/or secondary power sources 250, 255 has fallen below a predetermined power level. Accordingly, the power source switch 260 may be configured to switch connections between the circuits 205, 210, and 215 of the IMD 200 and the primary and secondary power sources 250, 255 based upon the power level being below the predetermined threshold value as determined by the sensor 265. In one embodiment, the predetermined threshold value may be a power level just above a remaining power level of zero (i.e., a dead battery).

For example, if the IMD 200 is transferring data between its communication interface circuit 215 and the data transfer device 235 (FIG. 2), and the power level sensor 265 determines that the power level of the secondary power source 255 is nearly depleted (i.e., below a predetermined threshold), the sensor 265 may send a control signal to the switch 260 to couple the primary power source 250 to the communication interface circuit 215 of the IMD 200 so as not to disrupt the data transfer. Similarly, if the power level within the primary power source 250 is determined to be depleted below a predetermined threshold, the power source switch 260 may switch the connections of the control circuit 205 and/or high output power circuit 210 to receive power from the secondary power source 255, as opposed to receiving power from the primary power source 250.

In an alternative embodiment, the power source switch 260 may include the circuitry to sense the power level remaining within the primary power source 250 and/or the secondary power source 255, and to switch connections between the circuits 205, 210, and 215 of the IMD 200 and the primary and secondary power sources 250, 255 based upon the sensed power levels. That is, the sensor 265 for sensing the remaining power level of the primary and secondary power sources 250, 255 may be an integral component of the power source switch 260 as opposed to being a separate component as illustrated in FIG. 14.

Although the present invention has been described with reference to preferred embodiments, it will be appreciated by those of ordinary skill in the art that a wide variety of alternate and/or equivalent implementations calculated to achieve the same purposes may be substituted for the specific embodiments shown and described without departing from the spirit and scope of the present invention.

What is claimed is:

1. A method for incorporating a power source in an implantable medical device, comprising the steps of:
    independently providing power to a control circuit by a first power source positioned within the device, the control circuit obtaining physiological data of a patient in which at least the control circuit is implanted;
    independently providing power to a communication circuit by a second power source positioned within the device; and
    sensing a remaining power level of the second power source, the first power source, or both first and second power sources to determine if the remaining power level of either the first or second power source has fallen below a predetermined threshold; and
    providing power to the control circuit and the communication circuit by a) the first power source if the remaining power level of the second power source has fallen below a predetermined threshold or b) the second power source if the remaining power level of the first rower source has fallen below a predetermined threshold.

2. The method of claim 1, further comprising:
    sensing a remaining power level of the second power source;
        determining if the remaining power level has fallen below a predetermined threshold; and
    providing power to the communication circuit by the first power source in response to determining that the remaining power level has fallen below the predetermined threshold.

3. The method of claim 1, further comprising:
    sensing a remaining power level of the first power source;
    determining if the remaining power level has fallen below a predetermined threshold; and
    providing power to the control circuit by the second power source in response to determining that the remaining power level has fallen below the predetermined threshold.

* * * * *

UNITED STATES PATENT AND TRADEMARK OFFICE
CERTIFICATE OF CORRECTION

PATENT NO. : 7,657,315 B2  Page 1 of 1
APPLICATION NO. : 11/622313
DATED : February 2, 2010
INVENTOR(S) : Schmidt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 371 days.

Signed and Sealed this

Thirtieth Day of November, 2010

David J. Kappos
*Director of the United States Patent and Trademark Office*